(12) United States Patent
Lee

(10) Patent No.: US 10,946,146 B2
(45) Date of Patent: Mar. 16, 2021

(54) SYRINGE DRIVING APPARATUS AND SYSTEM

(71) Applicant: EPIC MEDICAL PTE LTD, Singapore (SG)

(72) Inventor: Freddie Eng Hwee Lee, Singapore (SG)

(73) Assignee: EPIC MEDICAL PTE. LTD., Singapore (SG)

( * ) Notice: Subject to any disclaimer, the term of this patent is extended or adjusted under 35 U.S.C. 154(b) by 337 days.

(21) Appl. No.: 15/848,528

(22) Filed: Dec. 20, 2017

(65) Prior Publication Data

US 2018/0177954 A1 Jun. 28, 2018

Related U.S. Application Data

(60) Provisional application No. 62/437,918, filed on Dec. 22, 2016, provisional application No. 62/479,606, filed on Mar. 31, 2017.

(51) Int. Cl.
*A61M 5/315* (2006.01)
*A61M 5/145* (2006.01)
*A61M 5/20* (2006.01)
*A61M 39/28* (2006.01)

(52) U.S. Cl.
CPC ...... *A61M 5/31571* (2013.01); *A61M 5/1454* (2013.01); *A61M 5/2033* (2013.01); *A61M 39/28* (2013.01); *A61M 2005/2073* (2013.01); *A61M 2205/0216* (2013.01)

(58) Field of Classification Search
CPC ............ A61M 5/31571; A61M 5/1454; A61M 5/2033; A61M 2005/2073; A61M 2005/2026; A61M 39/28
See application file for complete search history.

(56) References Cited

U.S. PATENT DOCUMENTS 5,318,539 A 6/1994 O'Neil
2012/0330275 A1* 12/2012 Rude ................. A61M 5/20
604/506

FOREIGN PATENT DOCUMENTS

EP 2898910 A1 7/2015
EP 3281659 A1 2/2018
WO WO 2015/166286 A2 11/2015

OTHER PUBLICATIONS

European Patent Application No. 17209918.6; Extended Search Report; dated May 16, 2018; 8 pages.

* cited by examiner

*Primary Examiner* — Laura A Bouchelle
*Assistant Examiner* — Anh Bui
(74) *Attorney, Agent, or Firm* — BakerHostetler

(57) ABSTRACT

A syringe driving apparatus includes a housing, a driving member disposed in the housing and a resilient member connected to the housing and the driving member. The housing having a front end, a back end and a compartment between the front end and the back end, the compartment is configured to receive a plunger of the syringe therein. The driving member is movable relative to the housing between the front end and the back end. Movement of the driving member towards the back end deforms the resilient member to store potential energy in the resilient member, and upon release of the potential energy, the resilient member moves the driving member towards the front end to press the plunger to expel medicine out of the syringe.

18 Claims, 23 Drawing Sheets

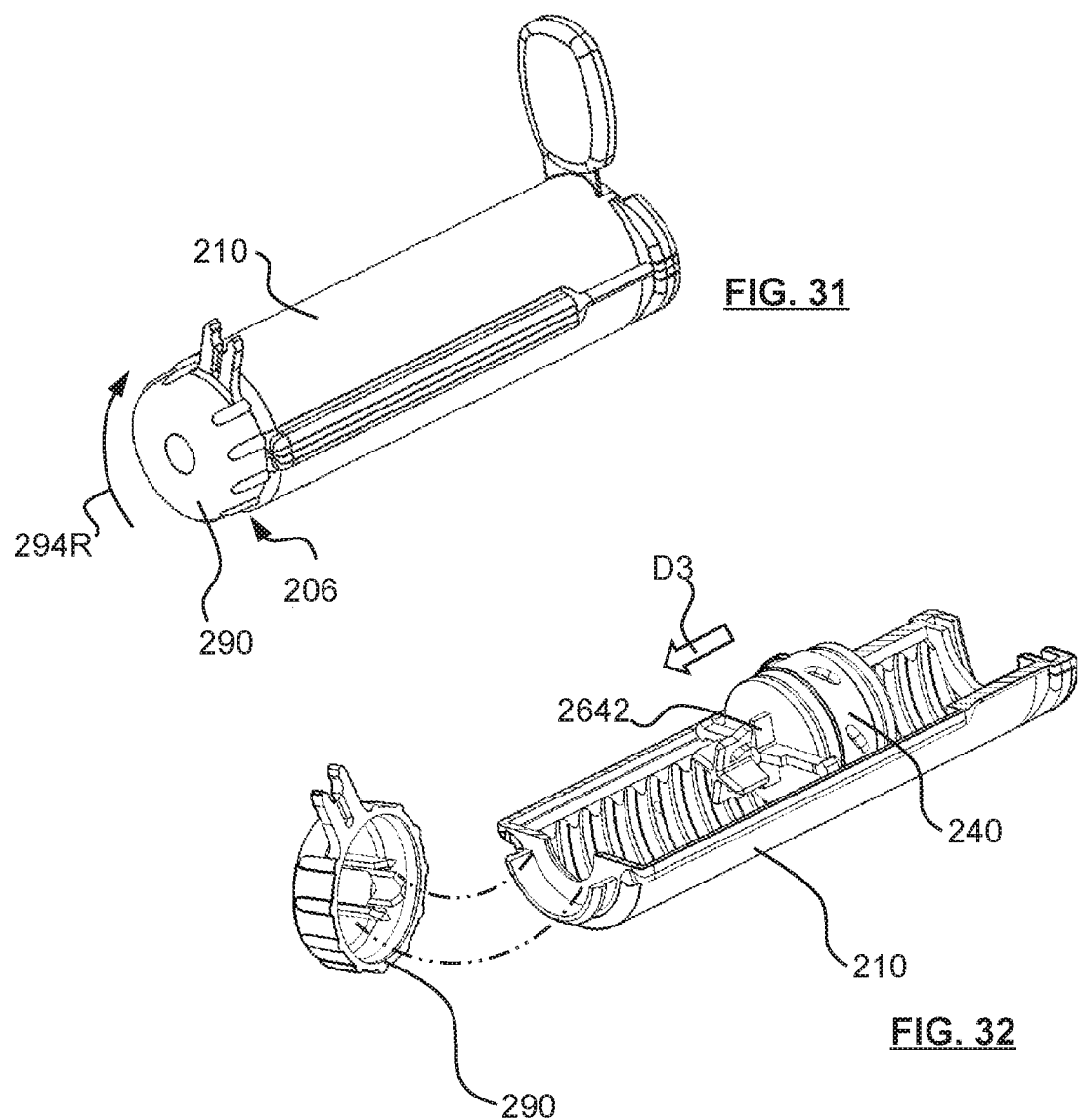
FIG. 31
FIG. 32
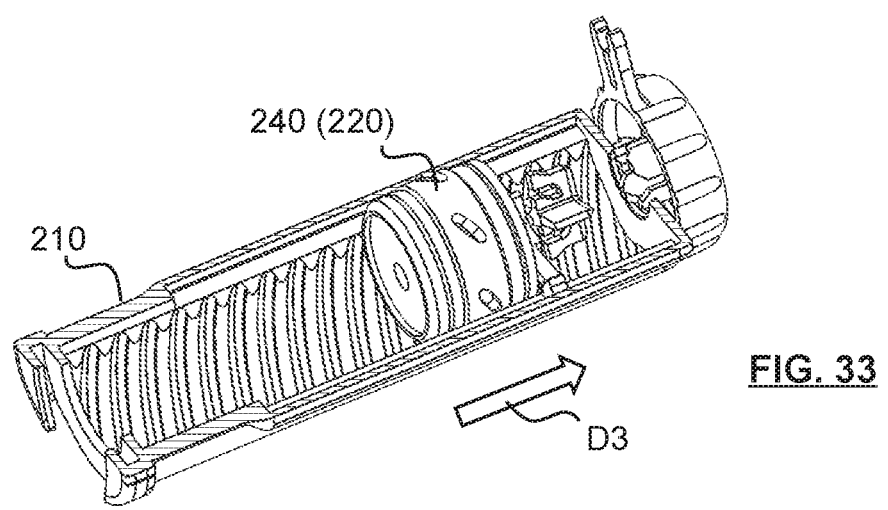
FIG. 33

SYRINGE DRIVING APPARATUS AND SYSTEM

CROSS-REFERENCE TO RELATED APPLICATIONS

This application claims priority to U.S. Provisional Patent Application Ser. No. 62/437,918 filed on Dec. 22, 2016, and U.S. Provisional Patent Application Ser. No. 62/479,606 filed on Mar. 31, 2017, the disclosure of which is hereby incorporated by reference as if set forth in its entirety herein.

TECHNICAL FIELD

The present disclosure relates to a syringe driving apparatus. In particular, it relates to a non-electrically powered syringe driving apparatus.

BACKGROUND

The use of syringes to push medication through an intravenous infusion (IV) line, commonly called IV push, is known for its benefits as it gives immediate and predictable therapeutic effects. Also, some medications can only be absorbed intravenously. Typically, the syringe is connected to the peripheral Intravenous Tubing Port (Y Site). Depending on the medication, the care giver has to consistently push the syringe from 2 mins to 10 mins to expel the contents. In addition to the challenge presented by a time deprived work schedule, the care giver has to administer the dose appropriate to the medication.

SUMMARY

The disclosed embodiments allow the care giver or nurse to execute the injection of fluids into the IV line automatically, by providing a syringe driving apparatus that is pre-calibrated to push the plunger of a filled syringe within the intended duration appropriate for the medicinal contents, typically 2 mins to 10 mins. The syringe driving apparatus has a housing to which a syringe is attachable, a driving member movably coupled to the housing, and a resilient member connected to the housing and the driving member. The syringe driving apparatus may be configured as a single use, disposable device in order to obviate the need for proper cleaning and maintenance. The apparatus is also quick and easy to operate, allowing easy and efficient time and work management.

Since the syringe driving apparatus is pre-calibrated with a predetermined fixed infusion rate for expelling the content of a connected syringe, the apparatus assists in ensuring compliance in administration duration with relevant standards. A pharmacy may prepare the prefilled syringe and dispense together with an appropriate syringe driving apparatus configured for the same infusion duration. Syringes and driving apparatus may be configured with respective codes, markings, labels etc., corresponding to different infusion duration, for easy identification and pairing. The nurse who uses the syringe for infusion together with the driving apparatus could check the pairing of syringe and contraption before connecting to patient, without having to actually push the syringe.

In the disclosed embodiments, the potential elastic energy of a deformed resilient member is used to push the plunger of a syringe attached to a syringe driving apparatus for automatic infusion.

In one embodiment, the resilient member is one or an array of elastic band(s) disposed in a chamber formed in a housing to which a movable or slidable puller or driving member is coupled. The puller enables the elastic bands to be stretched at a fixed elongation when it is pulled to a preset displacement. Upon release of the puller, the stretched elastic bands resume to its initial, non stretched length, forcing the puller to move back to the home or initial position. The puller may have a plunger seat rotatably coupled thereto, for receiving and engaging the syringe plunger. The movement or displacement of the puller in the direction towards the syringe barrel will exert the required force against the plunger to expel the fluid contents out of the syringe. With appropriate dimensioning of the elastic bands and the stretch or extension achieved by displacing the puller along axial direction of the housing, a required force required to expel the fluid contents for a specified duration can be attained.

The syringe driving apparatus allows the pushing of the syringe plunger to be activated upon demand only after a filled syringe is attached.

In one embodiment, the pushing action on the syringe plunger s initiated by breaking of the puller to unlock the actuator connected to the elastic band assembly. Without the resistance offered by the contents of the syringe, the actuator will move with a projectile like momentum away from the adjoining section of the puller. Alternatively, the actuator may be released to perform its function of pushing the syringe plunger by other configurations, such as a catch or latch that may subsequently be activated by pushing a button or other spring assisted means.

After completion of infusion, the syringe may be detached from the syringe driving apparatus by disengaging the flange of the syringe from the slots predisposed at the open end of the housing of the syringe driving apparatus.

The force generated by the stretched elastic bands is approximately proportional to its linear extension, hence provides a constant force profile that is operable over a range of fluid volumes for infusion.

Embodiments of the present disclosure allow combinations of elastic properties, shapes, dimensions to cumulatively result the desired force profile to push a syringe plunger.

In another embodiment, a syringe driving apparatus has a housing, a driving member movably disposed in the housing, and a resilient member connecting the housing to the driving member. The driving member has a casing and a slider movably disposed in the casing. The resilient member is a spiral spring disposed in the casing, with an inner end connected to the slider and an outer end connected to the casing. Movement of the slider along an axial direction of the housing towards the back end causes the casing to rotate to wind the spiral spring to store potential energy in the spiral spring, and upon release of the potential energy, the spiral spring unwinds to move the casing towards the front end to press the plunger for infusion.

BRIEF DESCRIPTION OF DRAWINGS

Embodiments disclosed therein are explained in conjunction with the figures, by way of example only, in which:

FIG. 31 is a perspective view of FIG. 25 showing twisting operation of the knob.

FIG. 32 is a perspective exploded view of FIG. 31 omitting the upper housing and the assembly of the knob and the housing.

FIG. 33 is a perspective exploded view of FIG. 31 omitting the upper housing and showing movement of the driving member toward the back end of the housing.

DETAILED DESCRIPTION OF PREFERRED EMBODIMENTS

Figure 1:
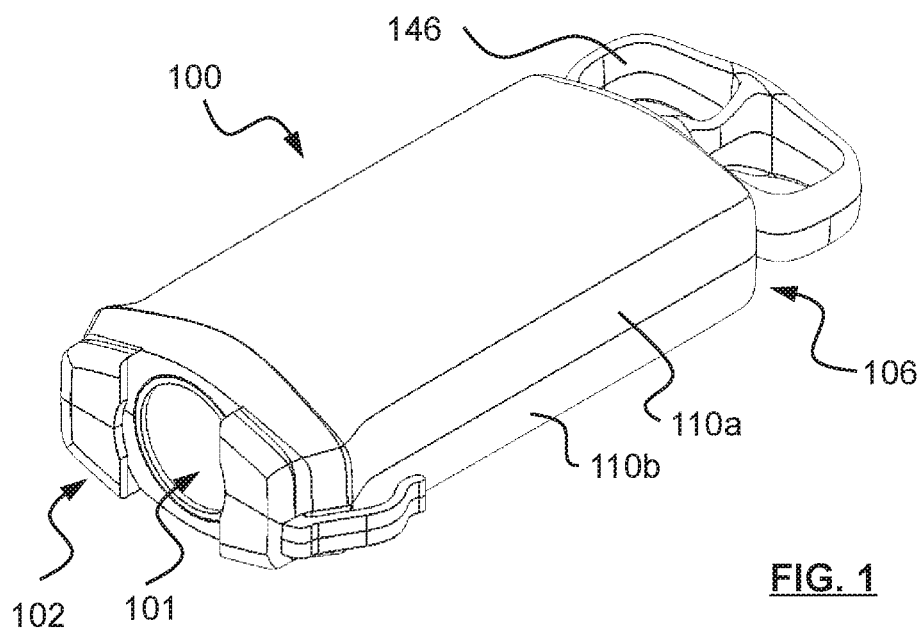
FIG. 1 is a perspective front view showing a syringe driving apparatus according to one embodiment of the present disclosure.
Figure 2:
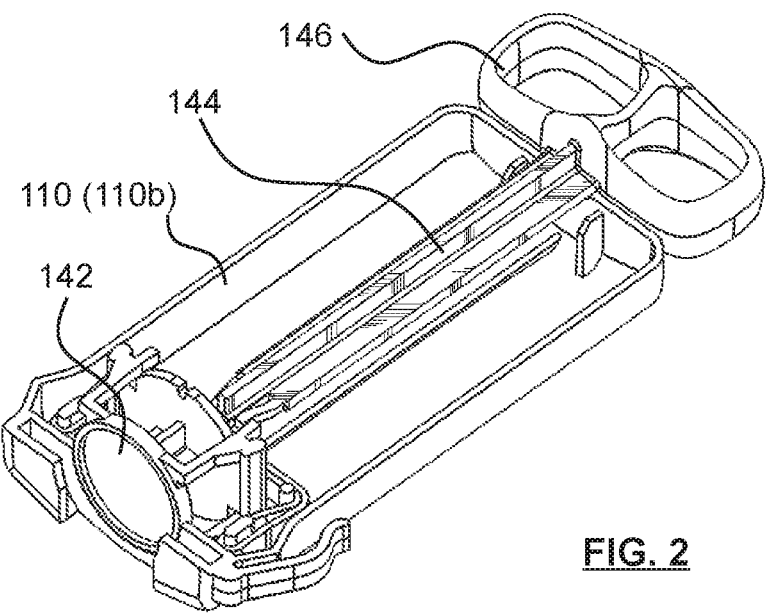
FIG. 2 is a perspective view of FIG. 1 with one part of the housing omitted showing internal structure and components of the apparatus.
Figure 3:
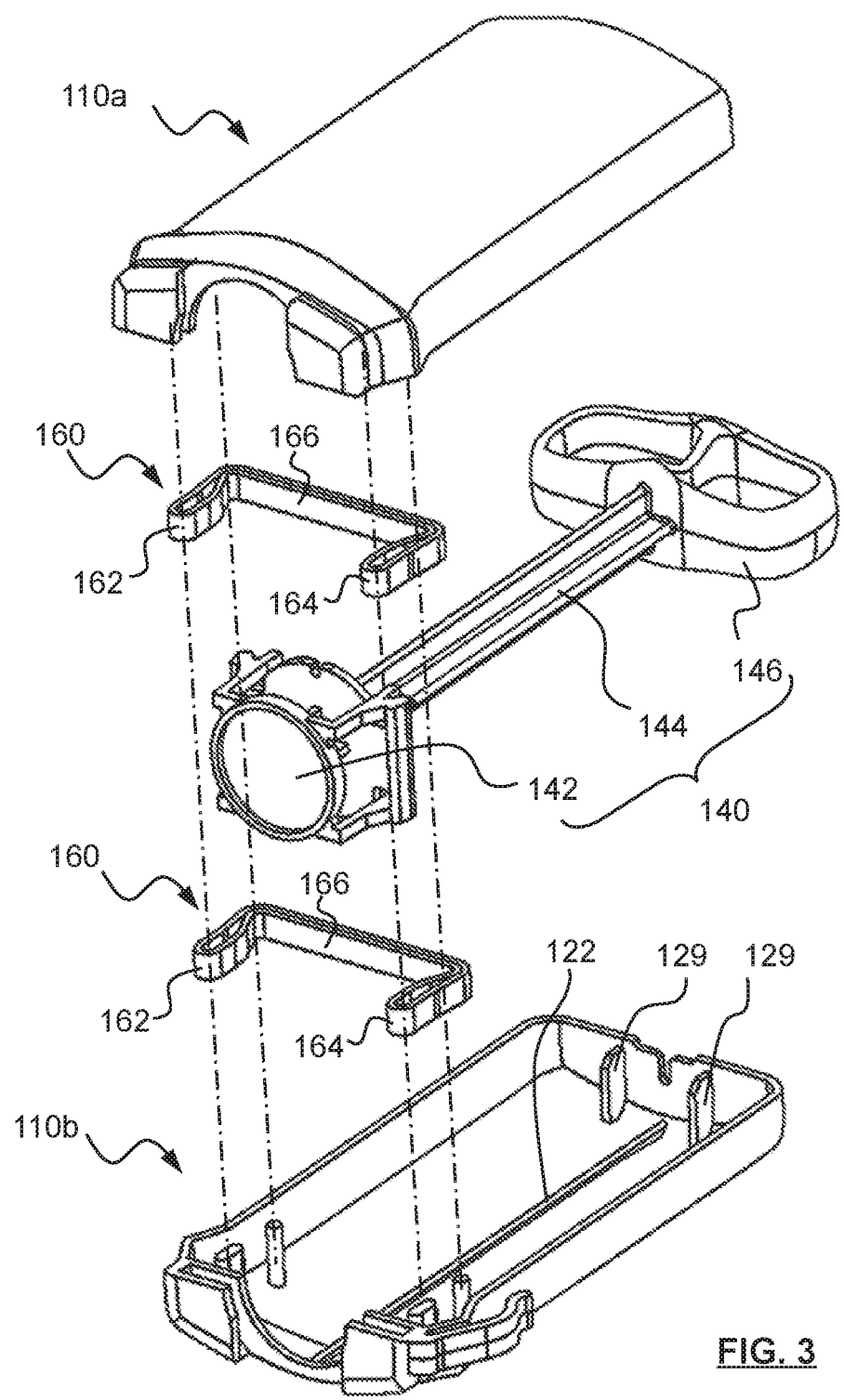
FIG. 3 is a perspective exploded view of FIG. 1.
Figure 4:
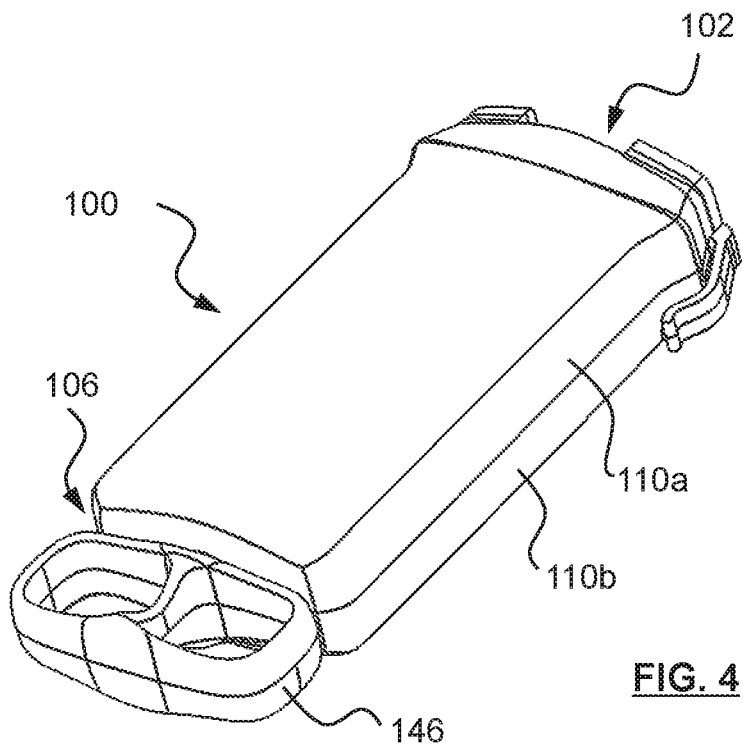
FIG. 4 is a perspective back view of FIG. 1.
Figure 5:
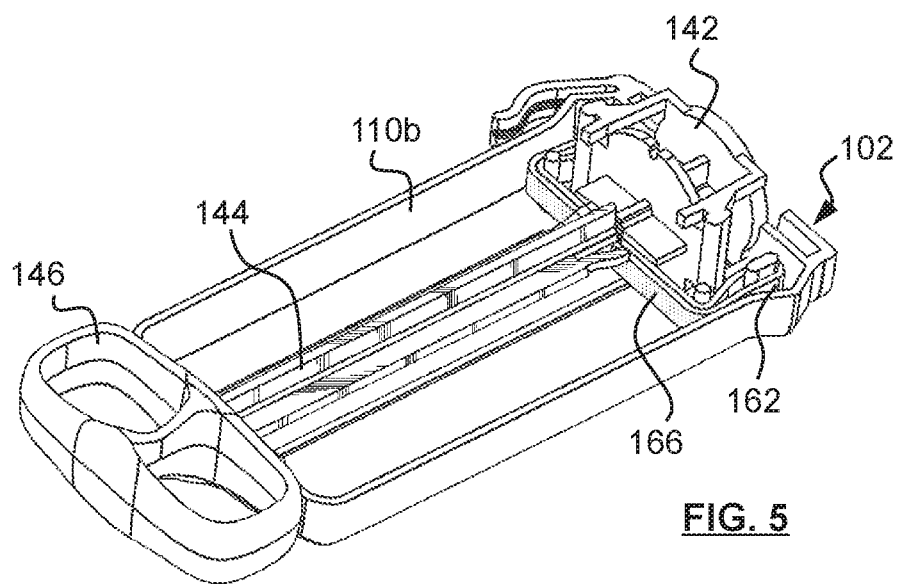
FIG. 5 is a perspective view of FIG. 4 with part of the housing omitted showing internal structure and components of the apparatus.

In one embodiment, the plunger of a syringe is pushed by the action of one or an array of elastic band(s) acting on an actuator of a driving member disposed in a housing of a syringe driving apparatus. The driving member is initially displaced by a pulling action of a puller/handle to which the actuator is removably coupled. The one or array of elastic band(s) are affixed to the housing by looping over pin like structures integrated within the housing, retains the driving member in a home or initial position in the proximity of the front end of the housing. The actuator is adjoined to the puller/handle at a neck portion that represents a weak breakable connection, which can be broken by a rotational twisting of the puller relative to the actuator.

The back end of the housing has a back opening with slits that act as guides in restricting the movement of the stem of the puller within a direction along its own axis when the puller is pulled in an outward direction by finger grips of an operator.

The elastic bands which are movably affixed to the housing and strapped on the actuator are stretched when the driving member is displaced away from the front end of the housing. The outward movement of the puller that caused the displacement of the actuator is limited by the vanes formed alongside the axially located actuator. The vanes are dimensioned larger than the opening of the slits. Upon the actuator reaching the second position, the flappable hook like arms or winglets on the puller stem pops up to the original position to abut against the rim of the slit, which prevents the puller stem from retracting back into the housing. The actuator is now locked to the back end of the housing, creating a volume space that accommodates the plunger of a filled syringe with its plunger extended out of the barrel of the syringe.

The front end of the housing has retaining features such as slots that engages the flange of the syringe, to secure the syringe to the driving apparatus. The stem is then detached from the actuator by a twisting action that breaks the neck portion between the actuator and the stem.

The one or array of elastic band(s) used in embodiments of the present disclosure may be fabricated from any stretchable material like isoprene, silicone or any elastic material.

Referring now to the drawings, according to one embodiment as shown in FIGS. 1 to 21, a syringe driving apparatus 100 includes a housing 110, a driving member 140 coupled to the housing 110, and one or more resilient members, e.g. elastic band(s) 160 connecting the driving member 140 to the housing 110. Housing 110 has a front end 102 and a back end 106. The front end 102 has a retaining portion 124 configured to receive and fix a flange 84 of a syringe 80 thereto. Housing 110 may include an upper portion 110*a* and a lower portion 110*b* which is/are generally and interchangeably referred to as housing in the context of this disclosure.

Driving member 140 has an actuator 142 disposed in the housing 110, a handle 146 disposed outside of the housing 110, and a stem 144 connecting the actuator 142 and the handle 146. Stem 144 is positioned to pass through a back opening 109 formed at back end 106 of housing 110.

Figure 6:
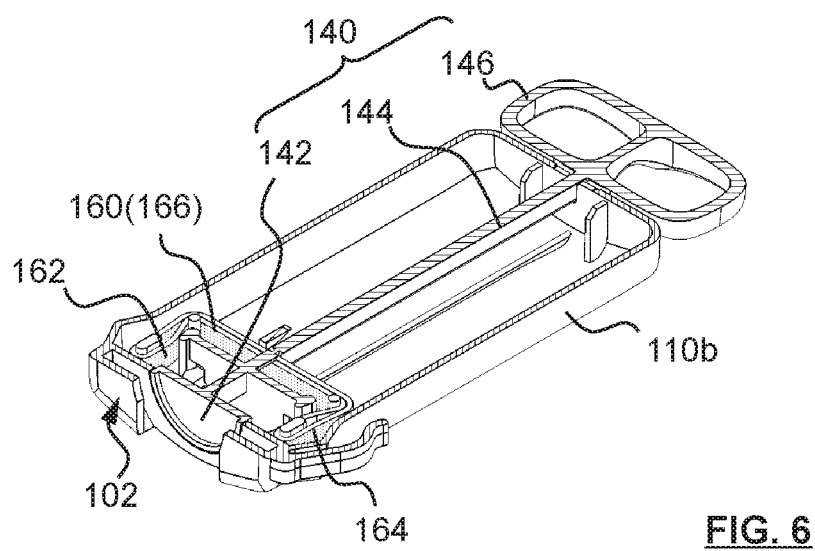
FIG. 6 is a cross sectional view of FIG. 1 when the actuator is at the first position.
Figure 7:
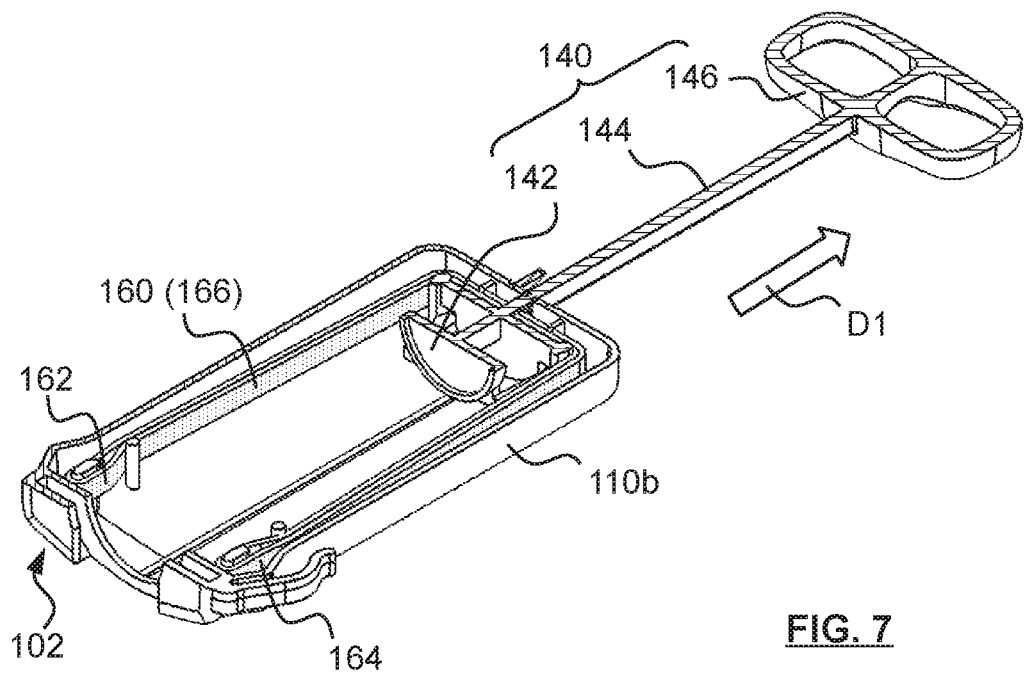
FIG. 7 is a cross sectional view of FIG. 1 when the actuator is at the second position.

Elastic band 160 has two fixing portions 162, 164 and a middle portion 166 between the two fixing portions 162 and 164. The two fixing portions 162, 164 are formed by looping the band 160 around the pin like features and fixed to the housing 110, and the middle portion 166 wraps around actuator 142 to urge the actuator 142 towards the front end 102 of housing 110. Driving member 140 is movable relative the housing 110 between a first position and a second position. When driving member 140 is at the first position, as shown in FIG. 6, elastic band 160 is less stretched, to keep the actuator 142 closer to the front end 102 of housing 110. Displacement of the driving member 140 towards the second position, e.g. along direction D1, as shown in FIG. 7, causes the elastic band 160 to become more stretched, and moves the actuator 142 away from the front end 102 of housing 110. When the actuator 142 is at the second position, the more stretched elastic band 160 stores elastic energy therein which, in turn, acts against the actuator 142 and creates a tendency to move the actuator 142 towards the front end 102 of housing 110.

Figure 8:
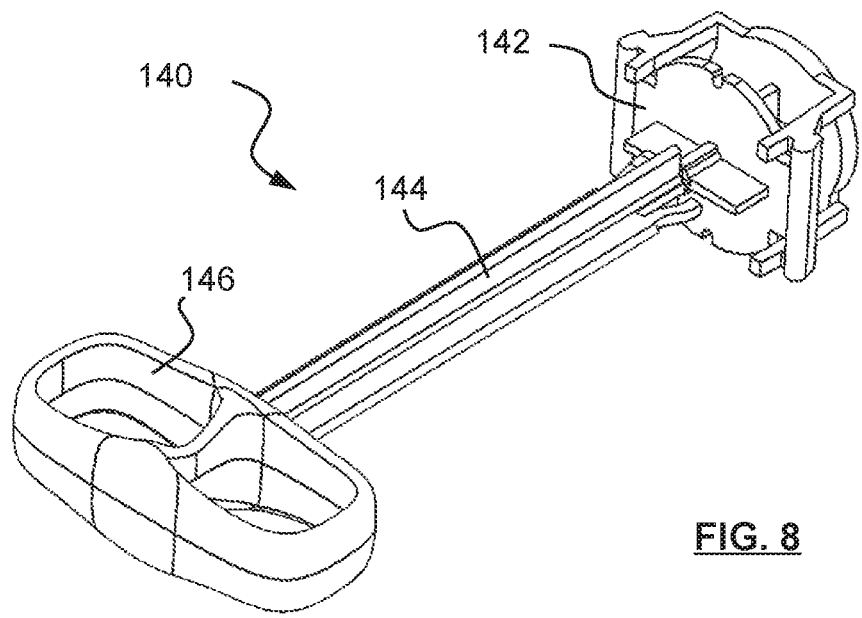
FIG. 8 is a perspective view of the driving member of the apparatus of FIG. 1.
Figure 9:
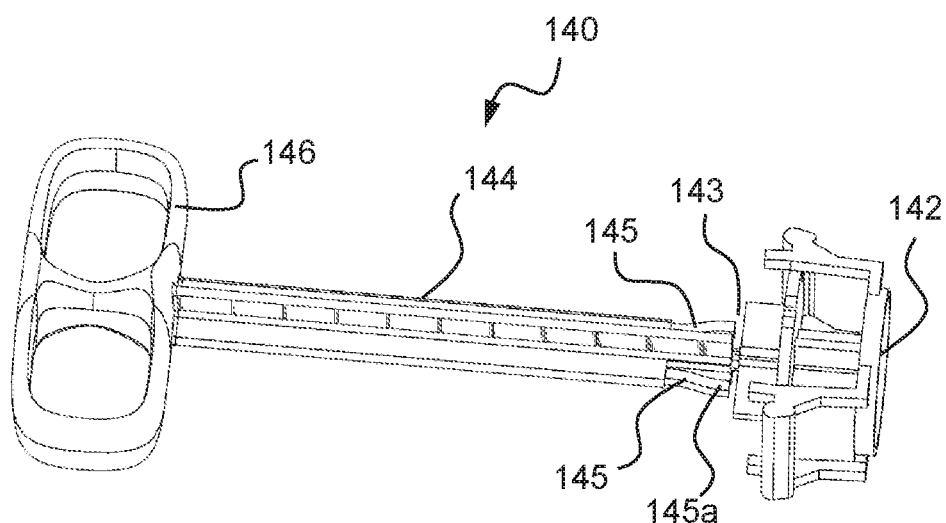
FIG. 9 is a perspective view of the driving member of FIG. 8 viewing from another angle.
Figure 10:
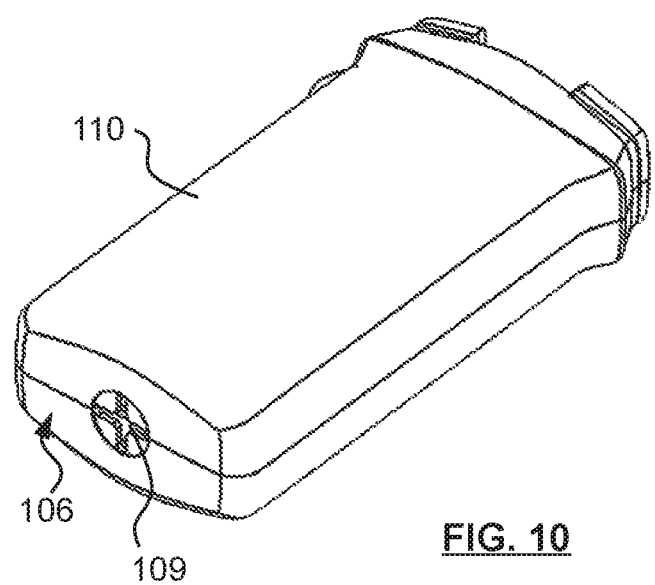
FIG. 10 is a perspective view of FIG. 4 omitting the driving member.
Figure 11:
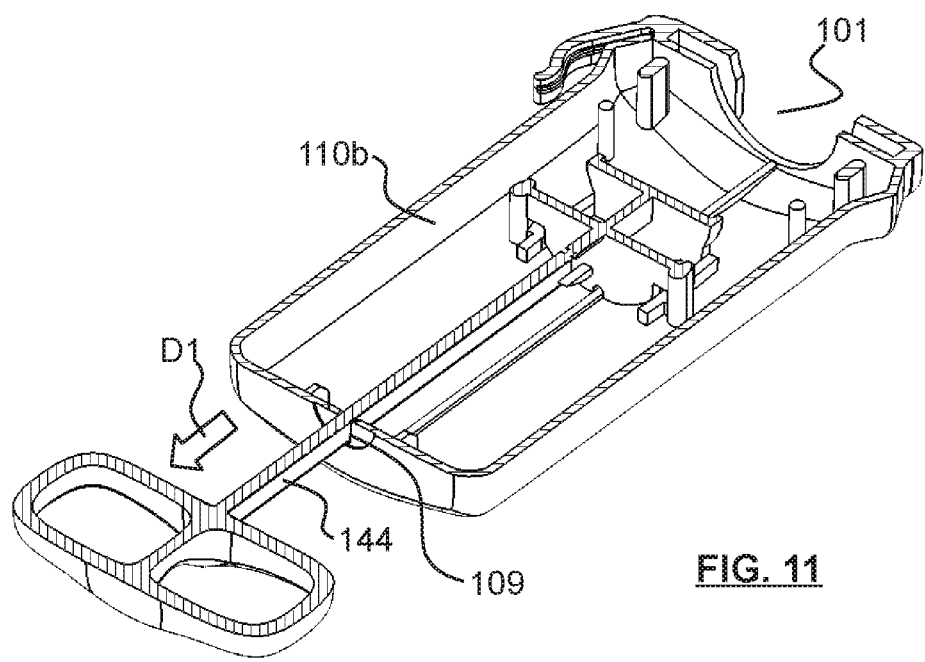
FIG. 11 is a perspective cross sectional view of FIG. 4 omitting the elastic band.
Figure 12:
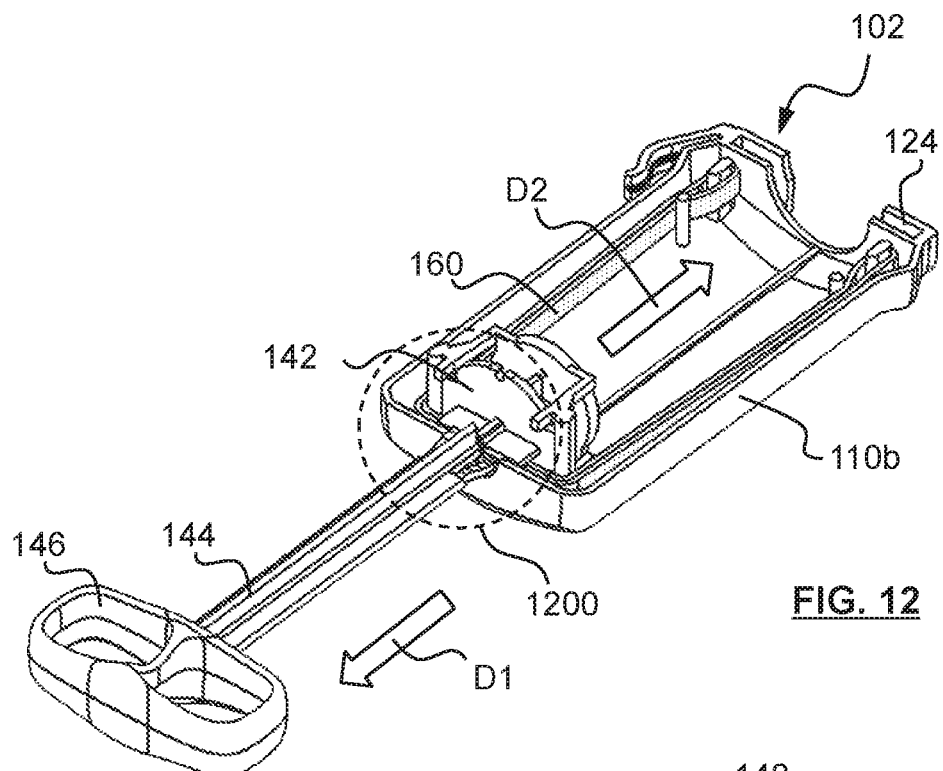
FIG. 12 is a perspective back view of FIG. 7.
Figure 13:
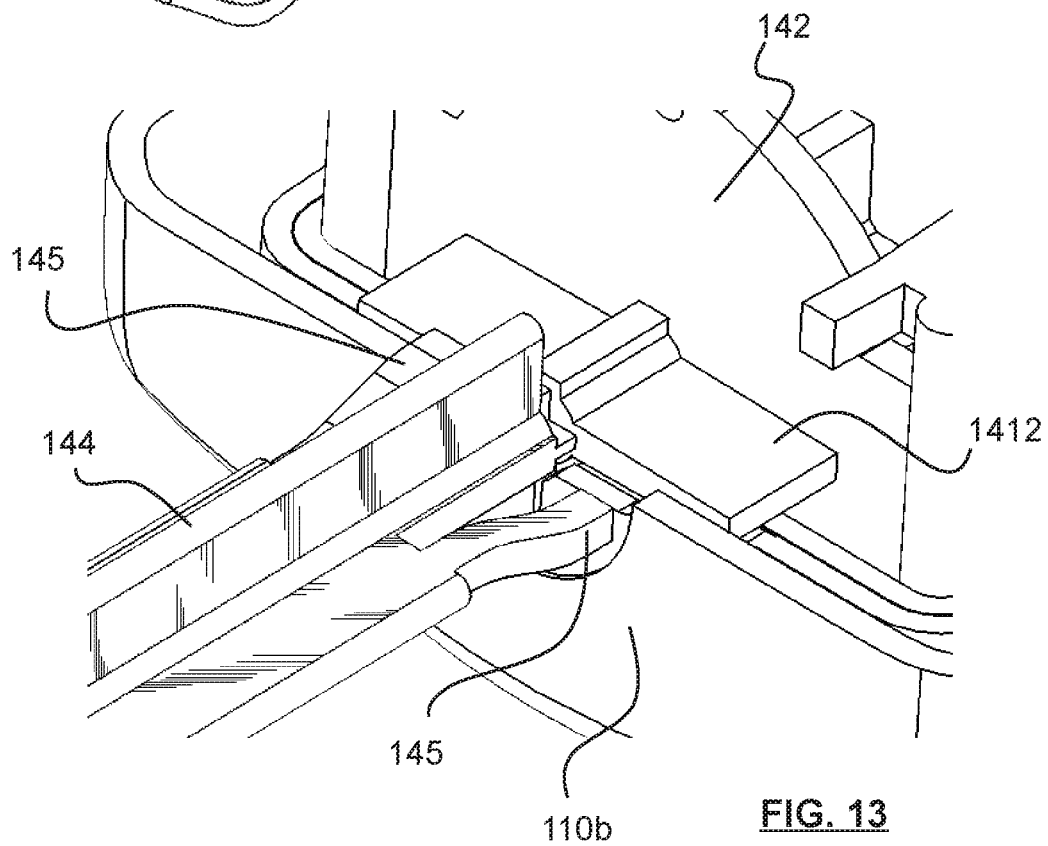
FIG. 13 is an enlarged partial view of FIG. 12.

As shown in FIGS. 8 and 9, driving member 140 is formed of an integral part, by injection molding for example. Between actuator 142 and stem 144 there is formed a neck portion 143. Neck portion 143 has a relatively lower strength compared to the actuator 142 and the stem 144, and is configured to present a lower resistance to shear forces and torsional moments. For example, neck portion 143 may have a cross sectional dimension less than that of the actuator 142 and the stem 144. As such, neck portion 143 forms a weak, breakable connection, which can be broken by a rotational twisting of the stem 144 relative to the actuator 142.

A pair of cantilever arms 145 are formed on the stem 144, adjacent to neck portion 143, and projecting slightly away from the stem 144 and towards the actuator 142. Cantilever arms 145 are elastically deformable with the free tip 145*a* flexing relative to the stem 144.

In use, stem 144 is moved along direction D1 (FIGS. 11, 12) away from housing 110, by e.g. a user gripping the handle 146 to pull the driving member 140 along direction D1, which displaces the actuator 142 away from the front end 102 of the housing 110. During the process of the driving member 140 being pulled along direction D1, the stem 144 slides along the back opening 109 formed on the back end 106 of the housing 110. Meanwhile, the actuator 142 stretches the elastic band 160 due the user's pulling force, resulting in elastic deformation of the elastic band 160 and potential elastic energy stored in the elastic band 160.

Figure 18:
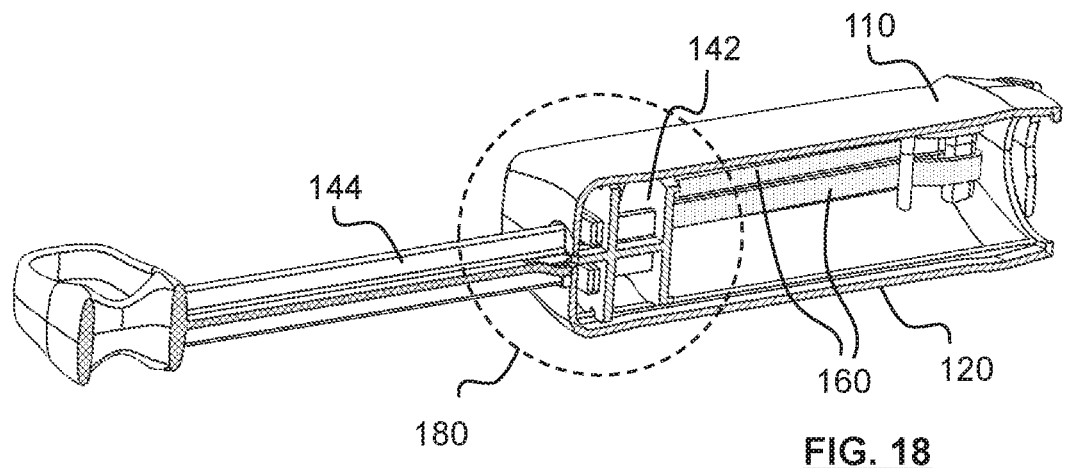
FIG. 18 is a perspective cross sectional view of FIG. 16B.
Figure 19:
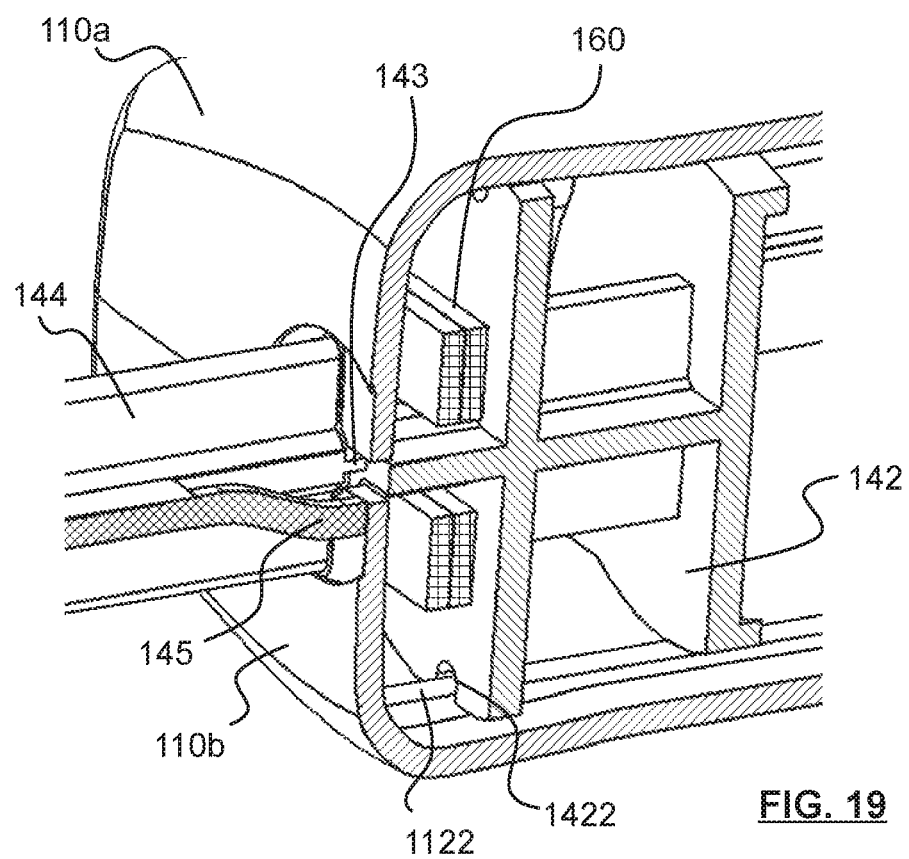
FIG. 19 is an enlarged partial view of FIG. 18.

As shown in FIGS. 18 and 19, housing 110 may have guide members such as ridge 1122 formed on the inner surface thereof, along axial direction of the housing 110. Actuator 142 may have notch 1422 of complementary shape and dimension as the ridge 1122, and engaged to ridge 1122 to assist and guide the displacement of the actuator 142 relative to the housing.

When the actuator 142 is displaced to a position closer the back end 106 of the housing 110, the cantilevered arms 145 are caused to flex inwardly towards the stem 144. Upon the actuator 142 reaching the second position, stem 144 is pulled completely out of the housing 100, and the cantilever arms 145 pass through the back opening 109 and resume the initial shape by flex outwardly away from the stem 114. The free end 145*a* of each cantilever arm 145 are positioned beyond the periphery of the back opening 109 and abut against the housing 110. Stem 144 is therefore prevented from retracting back into the housing 110 by which, the actuator 142 is locked at the second position. Meanwhile, the stretched elastic band 160 exerts a force against the actuator 142 in a direction D2 facing the front end 102 of the housing 110.

Actuator 142 may have vane 1412 formed adjacent to stem 144 to abut against the housing 110 (110*b*), to ensure the positioning of actuator 142 when the driving member 140 reaching the second position.

Figure 14:
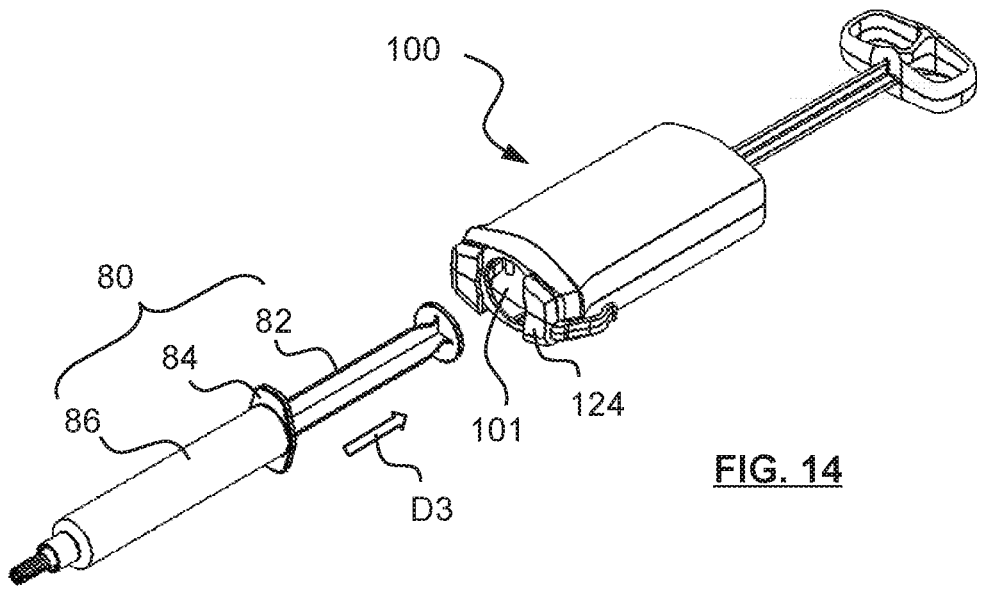
FIG. 14 is a perspective of the apparatus of FIG. 1 ready for receiving a syringe.
Figure 15:
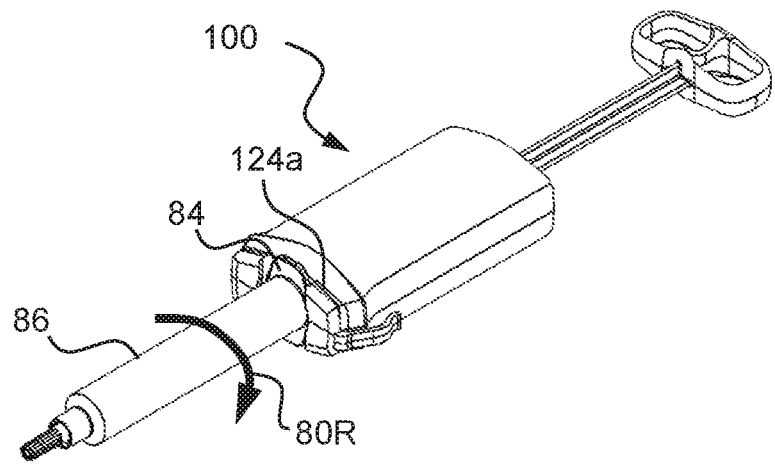
FIG. 15 is a perspective of the apparatus of FIG. 1 when a plunger of a syringe is inserted into the housing of the apparatus.
Figure 16A:
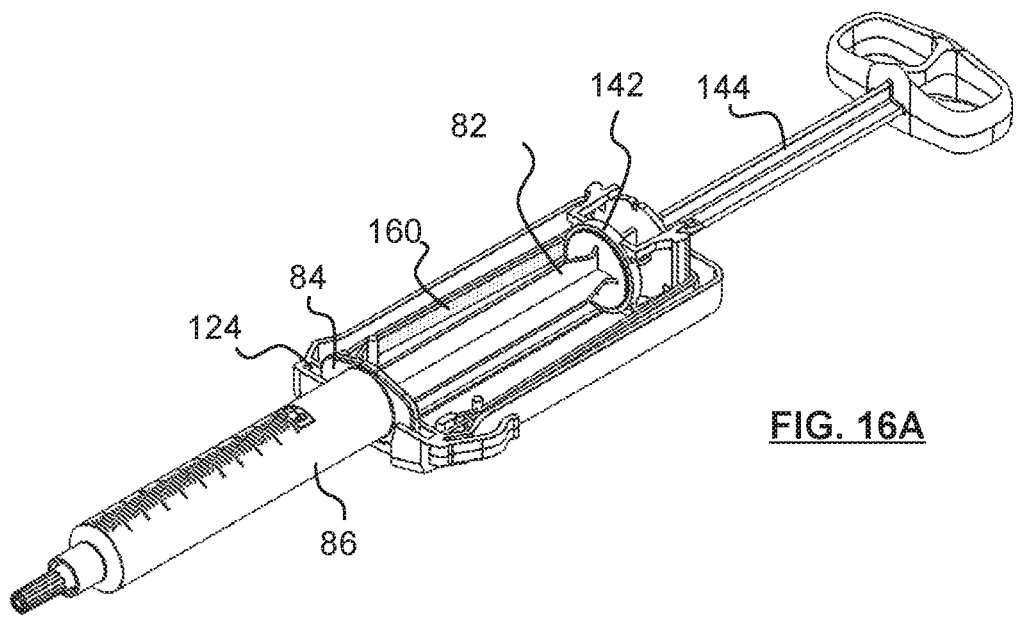
FIG. 16A is a perspective of the apparatus of FIG. 1 showing a plunger of a syringe is inserted into the housing of the apparatus and omitting the top portion of the housing.
Figure 16B:
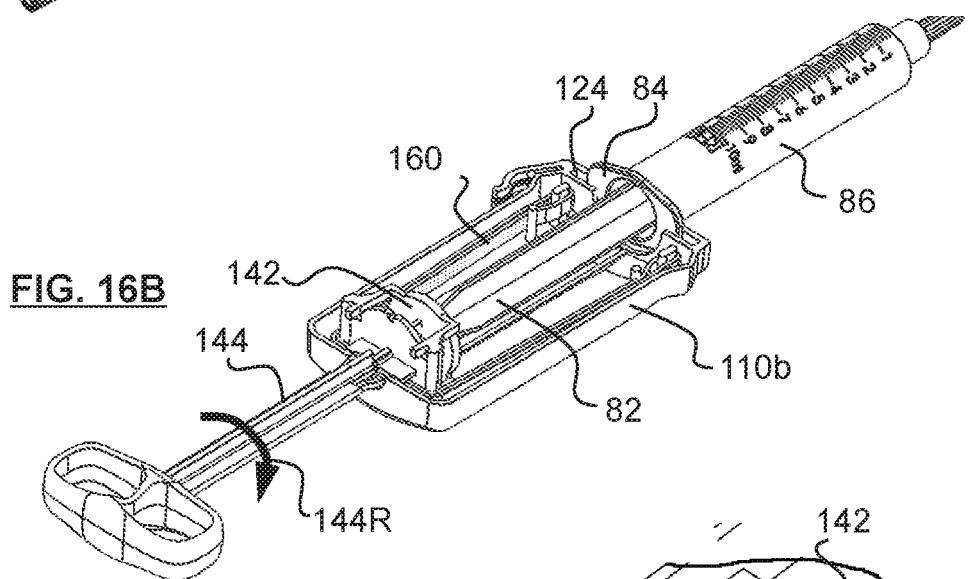
FIG. 16B is a perspective back view of FIG. 16A.
Figure 17:
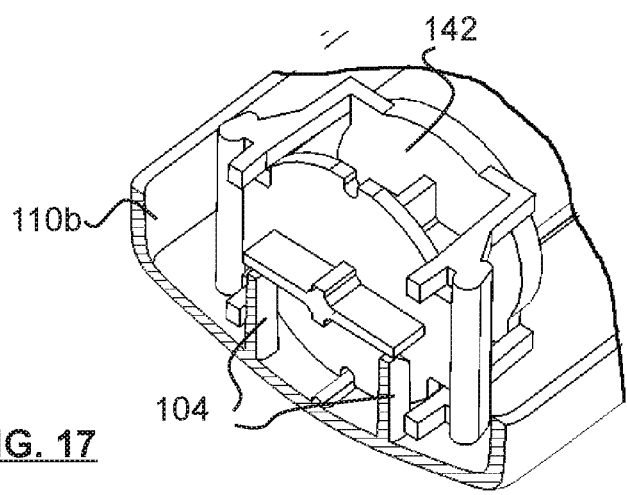
FIG. 17 is a partial cross sectional view of FIG. 16B.

As shown in FIGS. 14 and 15, when it is desired to carry out infusion operation, t a syringe 80 which is filled with liquid medication, is attached to the housing 110 with the plunger 82 inserted into the housing 110 through the front opening 101 at the front end 102 of the housing 110, along axial direction D3. The generally oval shaped flange 84 of the syringe barrel 86 is rotated to become aligned with the retaining portion 124 surrounding the front opening 101. When flange 84 is brought into contact with the rim of the front opening 101, the flange 84 is rotated along circular direction 80R, to position into the groove 124*a* of the retaining portion 124 to attach the syringe 80 to the apparatus 100.

The dimension of the housing 110 and the actuator 142 are configured in a manner such that when the portion of the plunger 82 extending out of the barrel 86 is fully received in the housing 110, the end surface 82*a* of the plunger 82 is in contact with or close proximity to the actuator 142, for example with a gap of about 0 to several mm therebetween.

Syringe 80 is now ready to be connected to a patient or is already connected, via appropriate tubes/conduits (not shown), for infusion of the medication filled in the syringe 80.

Figure 20:
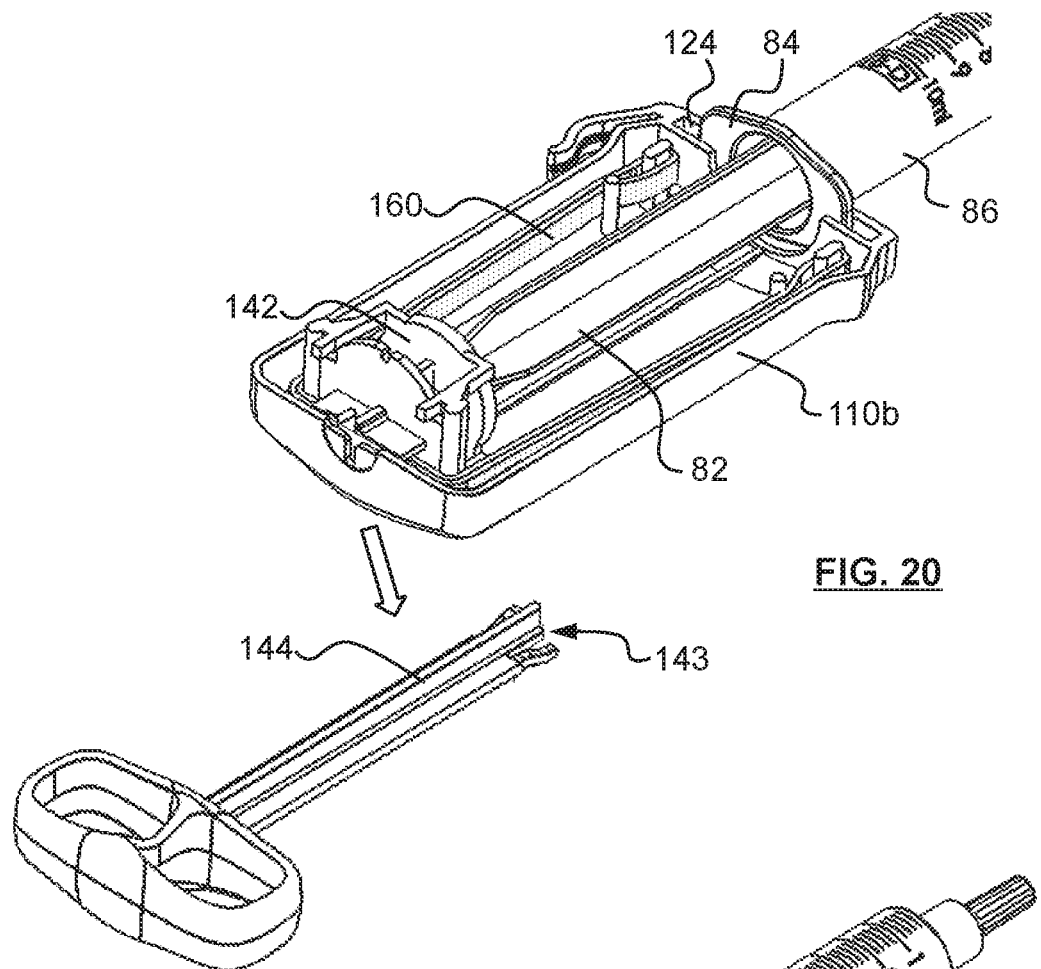
FIG. 20 is a perspective view showing the apparatus of FIG. 1 with a syringe attached thereto and ready for infusion operation via the syringe.

To start infusion, a user twists the handle 146 relative to the housing 110, causing the stem 144 together with the cantilevered arms 145 to become broken off from the actuator 142 at the neck portion 143, as shown in FIG. 20. To assist in easy operation of the stem 144 breaking off, housing 110 (110*b*) may have ribs 104 formed thereon that engages with the actuator 142 when the actuator 142 is at the second position (FIG. 17) to prevent actuator 142 from rotating during the twisting of the stem 144.

Figure 21:
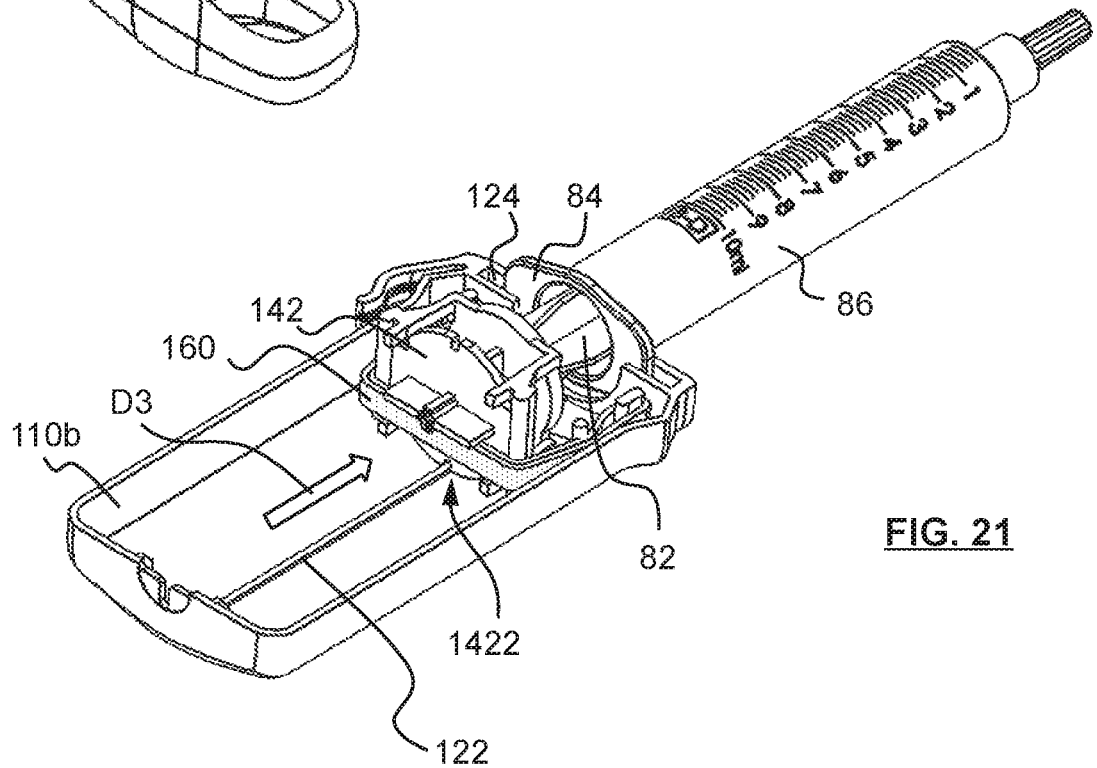
FIG. 21 is a perspective view showing the apparatus of FIG. 1 with a syringe attached thereto and after completion of the infusion operation.
Figure 22:
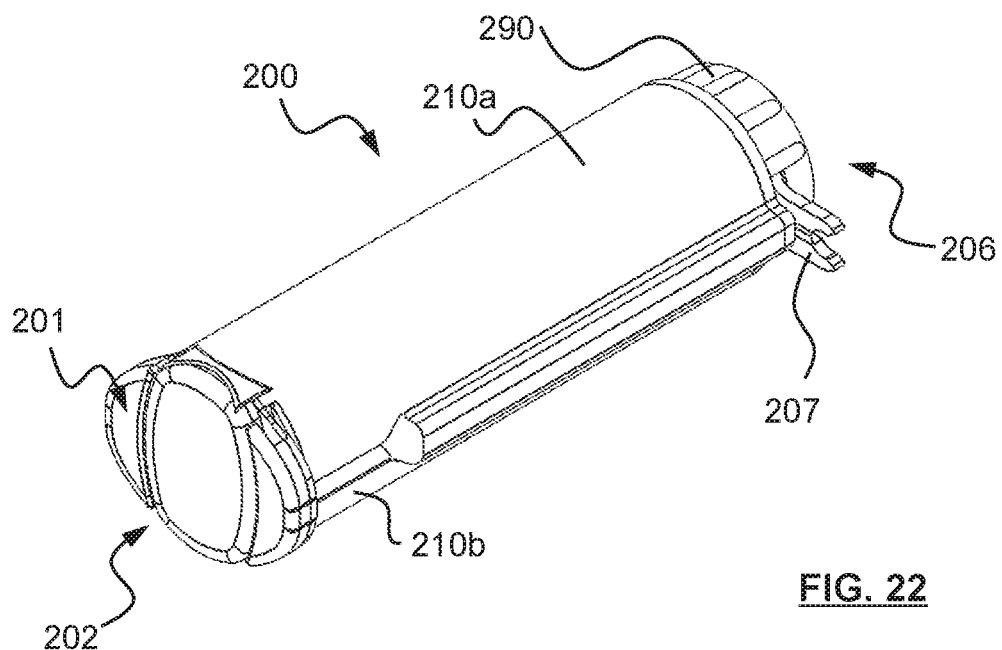
FIG. 22 is a perspective front view showing a syringe driving apparatus according to another embodiment of the present disclosure.
Figure 23:
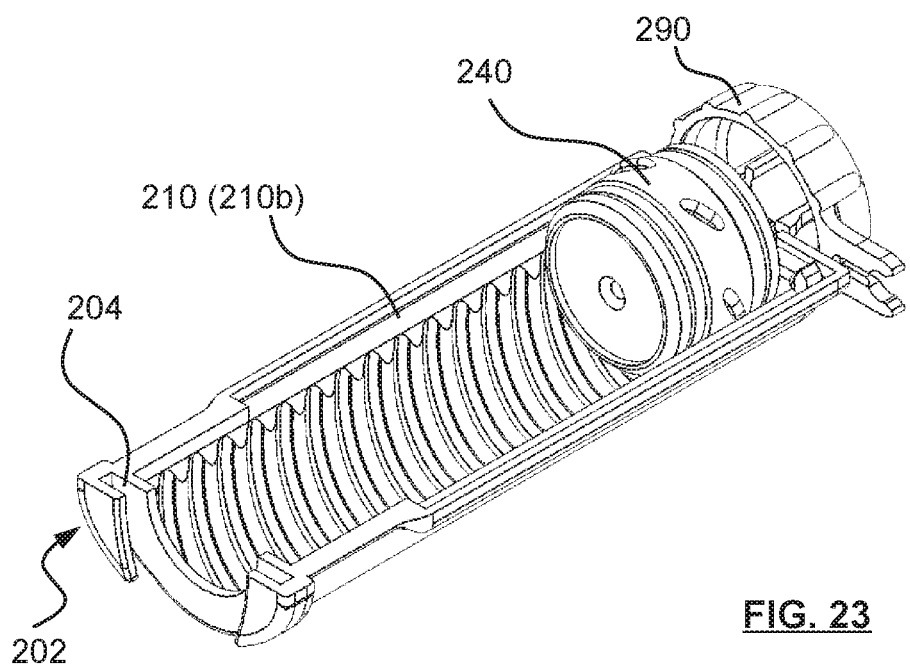
FIG. 23 is a perspective view of FIG. 22 with one part of the housing removed showing internal structure and components of the apparatus, in which the spring is in its winded state within the driving member.
Figure 24A:
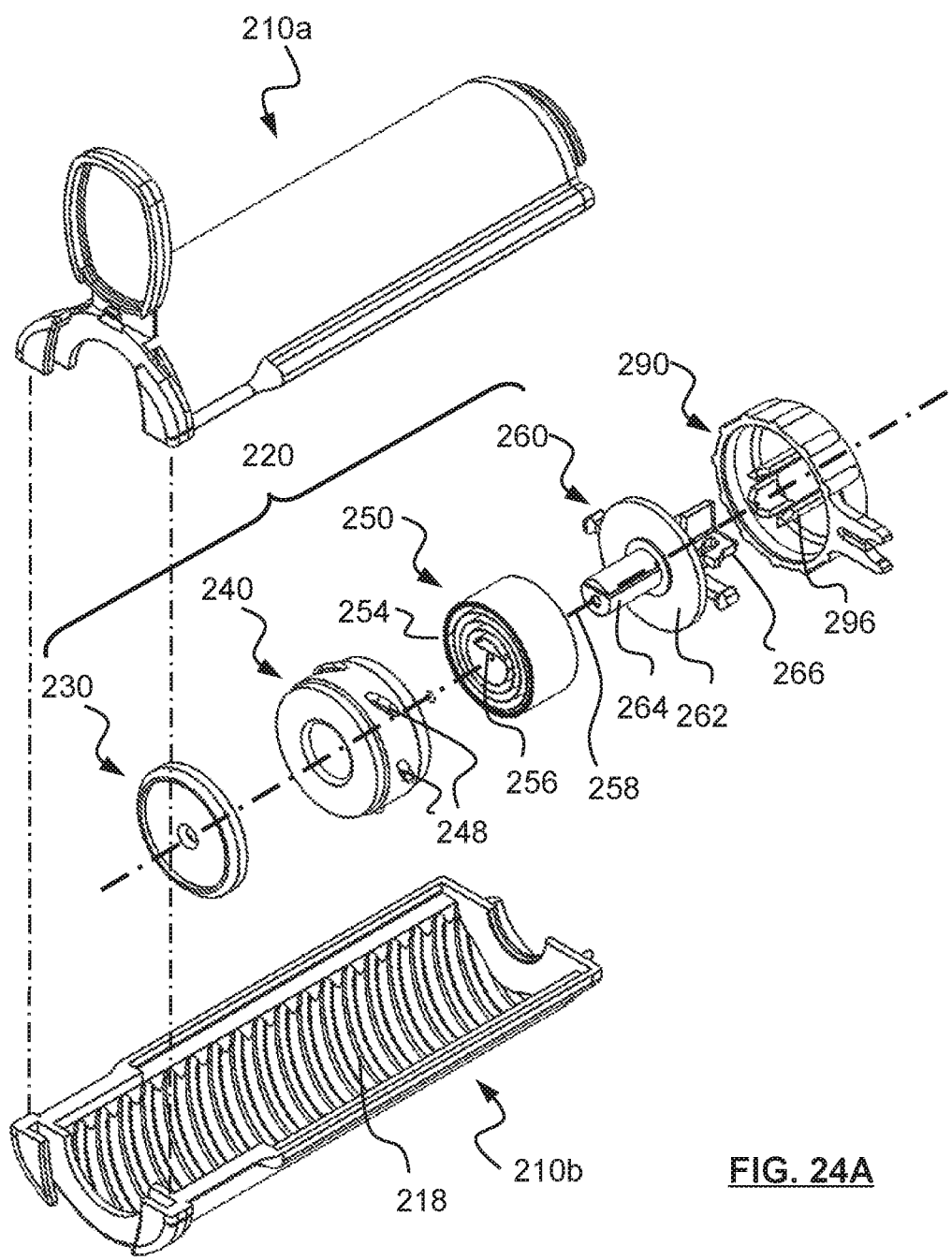
FIG. 24A is a perspective exploded front view of FIG. 22.
Figure 24B:
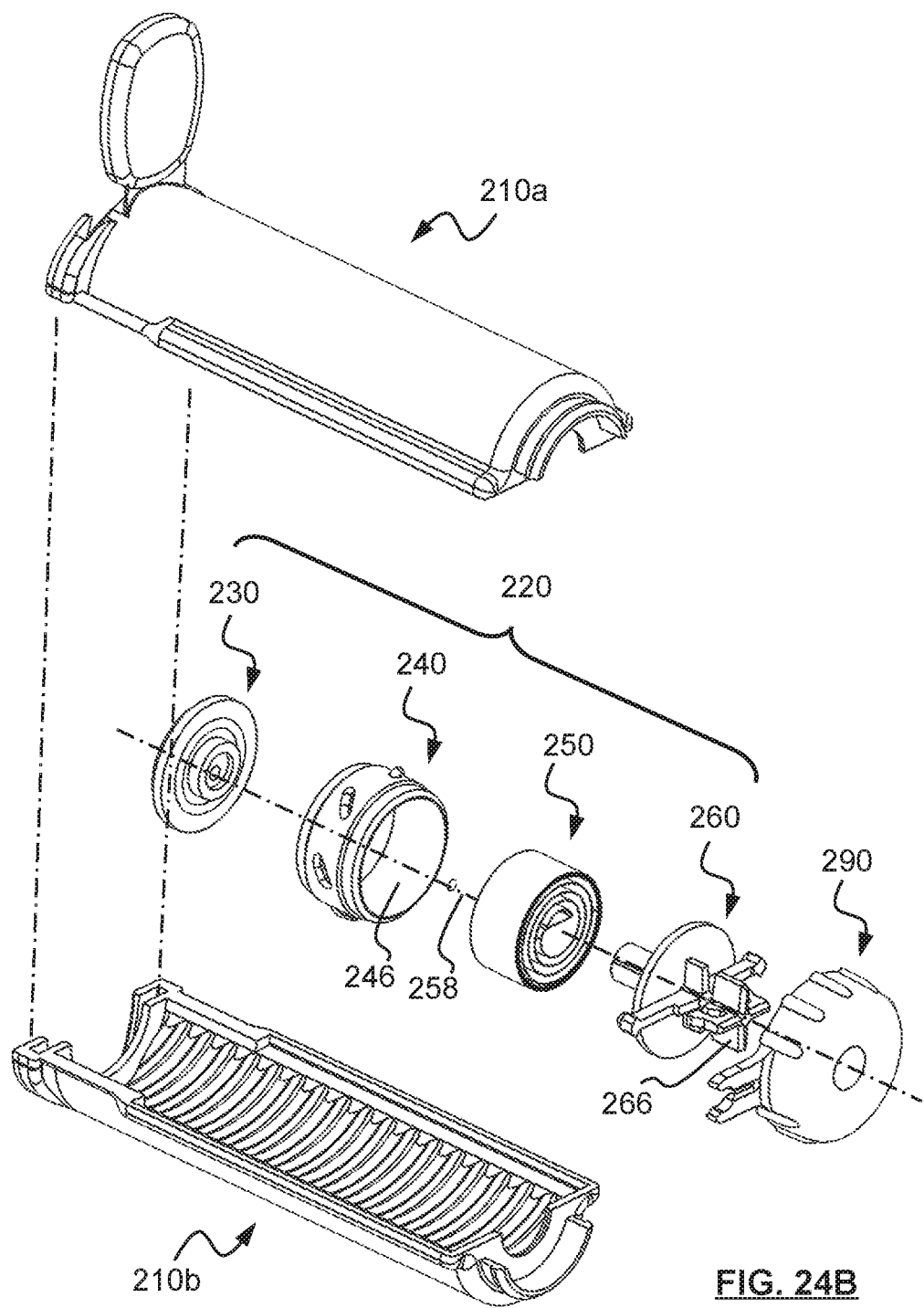
FIG. 24B is a perspective exploded back view of FIG. 22.
Figure 25:
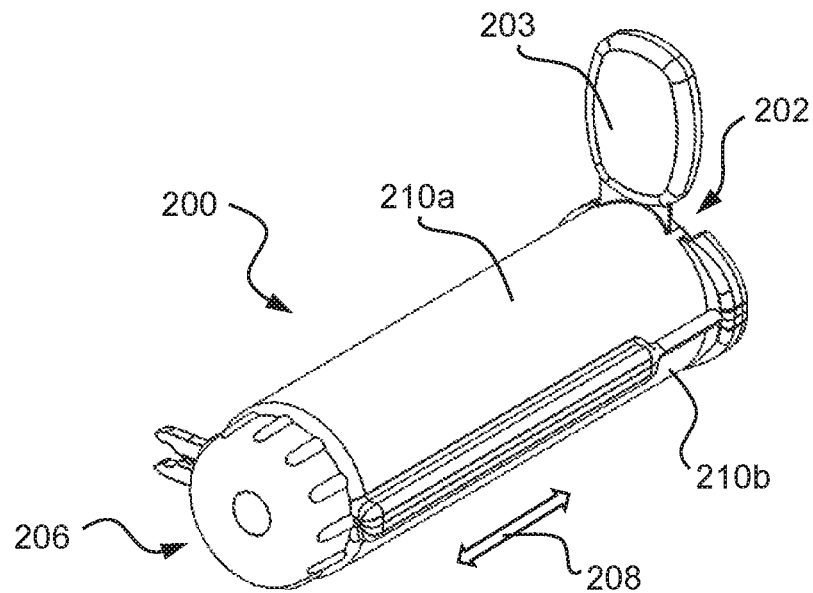
FIG. 25 is a perspective back view of FIG. 22.
Figure 26:
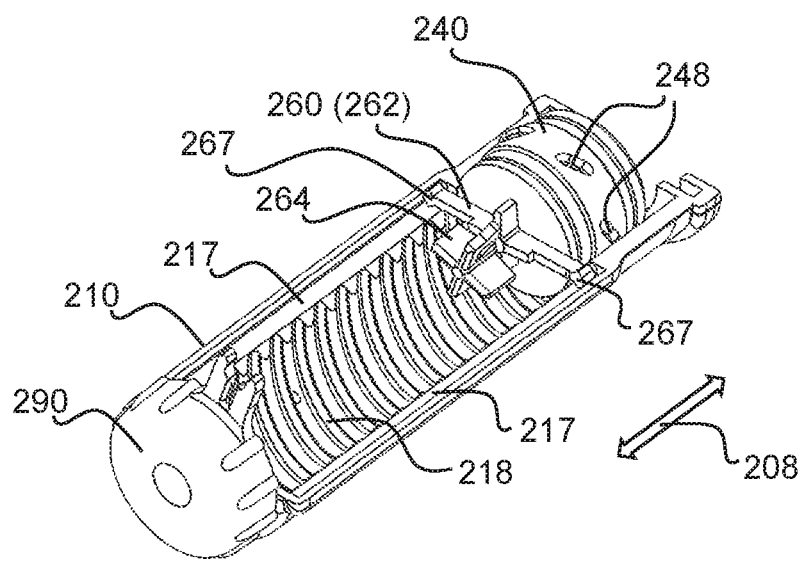
FIG. 26 is a perspective view of FIG. 25 with one part of the housing omitted showing internal structure and components of the apparatus, in which the spring has been released by a twisting action on the release knob.
Figure 27:
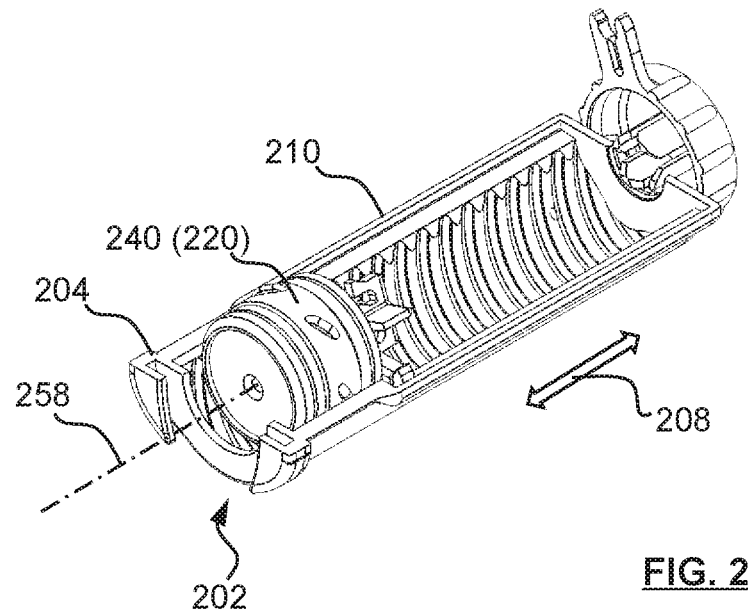
FIG. 27 is a perspective front view of FIG. 22 with one part of the housing omitted showing internal structure and components of the apparatus, where the driving member is positioned adjacent to the front end of the housing.
Figure 28:
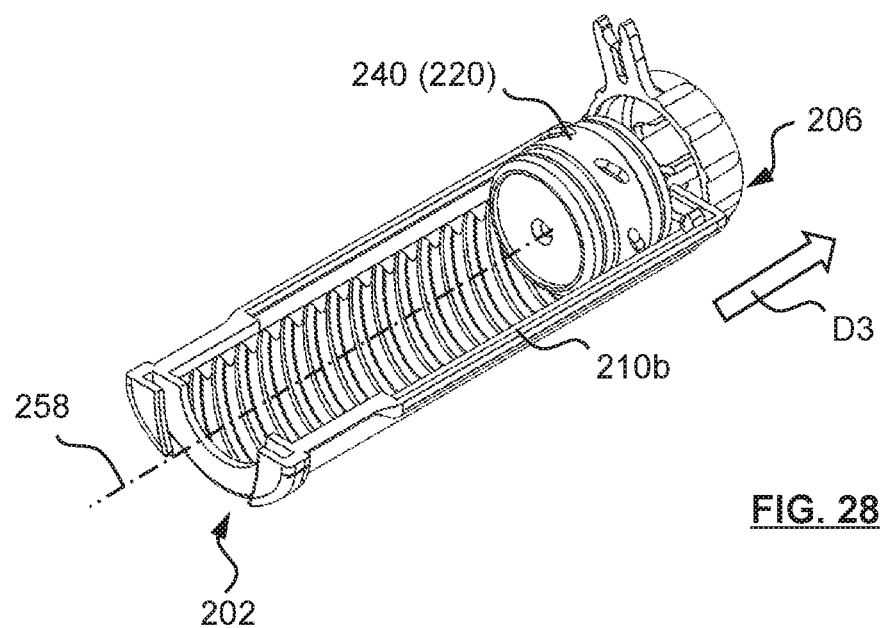
FIG. 28 is a perspective front view of FIG. 22 with one part of the housing omitted showing internal structure and components of the apparatus, where the driving member is moved to the back end of the housing.

Upon the stem 144 and the cantilever arms 145 being broken off from the actuator 142, the actuator 142 is unlocked from the housing 110, allowing the potential energy stored in the elastic band 160 to release which, in turn, brings the actuator 142 into abutment with the plunger 82. Continuous release of the potential energy from the elastic band 160 presses the actuator 142 against the plunger 82. Plunger 82 is then forced to move into the barrel 86 to expel the liquid medication out of the syringe 80 for infusion, as shown in FIG. 21.

In another embodiment, the plunger of a syringe is pushed by the action of a spiral or clock spring acting on a casing that is an integral part of a driving member e.g. a bobbin assembly installed within a housing of the apparatus. The driving member is initially displaced axially along the inner volume space of the housing such that the spiral spring within the casing is winded by the rotation of the casing. The driving member includes a slider movably coupled to the casing. The slider has a shaft to which one end of the spiral spring is affixed. Another end of the spiral spring is affixed to the casing.

The housing has helical grooves formed on the inner surface. The casing has ridges formed on the outer surface. The ridges engage with the helical grooves such that linear movement of the casing towards the back end of the housing along the longitudinal axis of the housing rotates to the casing about the longitudinal axis to wind the spiral spring. Unwind of the spiral spring causes the rotational movement of the casing relative to the housing about the longitudinal axis, and brings the casing to move linearly along the axial direction back to the front end of the housing.

The driving member is initially located at the open end/front end of the housing and a linear displacement of the driving member towards the opposite, back end of the housing will rotate the casing relative to the housing. Rotation of the casing causes the spring to wind, to store elastic potential energy in the spiral spring. The driving member is held at the end of the housing by a release knob that catches on to the stem like protrusion located at the frame of the slider. The stem has a neck portion that represents a weak breakable connection, which can be broken by a rotational twisting of the release knob relative to the frame.

Referring now to FIGS. 22 to 42, a syringe driving apparatus 200 includes a housing 210, a driving member or bobbin assembly 220 coupled to the housing 210, and a knob 290 for connecting, locking and releasing the driving member or bobbin assembly 220 to/from the housing 210. Housing 210 has a front end 202 and a back end 206. The front end 202 has a retaining portion 204 configured to receive and fix a flange 84 of a syringe 80 thereto. Housing 210 may include an upper portion 210a and a lower portion 210b which is/are generally and interchangeably referred to as housing in the context of this disclosure. Housing 210 may include a movable flap 203 adjacent to the front end 202 to cover the front opening 201 for, e.g. dust-proof purpose.

Driving member or bobbin assembly 220 includes a casing 240, a slider 260 coupled to casing 240, a shaft 266 formed on the slider 260 having a frame 262 engaged to housing 210 and disposed in the casing 240, and a spiral spring 250 disposed in the casing 240. Driving member 220 may optionally include a seat plate or disc 230 rotatably attached to the slider 260. An inner end 256 of the spiral spring 250 is fixed to the shaft 266, and an outer end 254 of the spiral spring 250 is fixed to the inner slot 246 of the casing 240. The knob 290 is attached to the back end 206 of housing 210, and is rotatable relative to housing 210. The slider 260 has a stem 264 that has features to enable its fitting with the tubular catch 296 disposed on the inner side of the knob 290. Stem 264 is positioned to pass through a back opening 209 formed at back end 206 of housing 210.

Apparatus 200 may include a clip 207 formed on the housing 210 for attaching the apparatus 200 to an Intravenous (IV) line so that the apparatus 200 can stay in place before, during and/after the infusion operation. Clip 207 may also be used to pinch the IV line if needed during operation. Clip 207 may be formed integral to knob 290. Alternatively, clip 207 may be formed as an integral to housing 210 or other portion of the apparatus 200, or a separate part assembled to the housing 210 or other parts of the apparatus 200.

As shown in FIGS. 24A, 24B, 25 and 26, the housing 210 has one or more helical grooves 218 formed on the inner surface thereof. The casing 240 has ridges 248 formed on the outer side surface thereof. Ridges 248 engage the helical grooves 218 to enable simultaneous rotational and axial movement of the casing 240 relative to the housing 210. Due the engagement of the ridges 248 and grooves 218, movement of the casing 240 along axial direction 208 of housing 210 from the front end 202 toward the back end 206 of the housing 210 rotates the casing 240 to wind the spiral spring 250 with respect to a spring axis 258, to store potential energy in the spiral spring 250.

Figure 29:
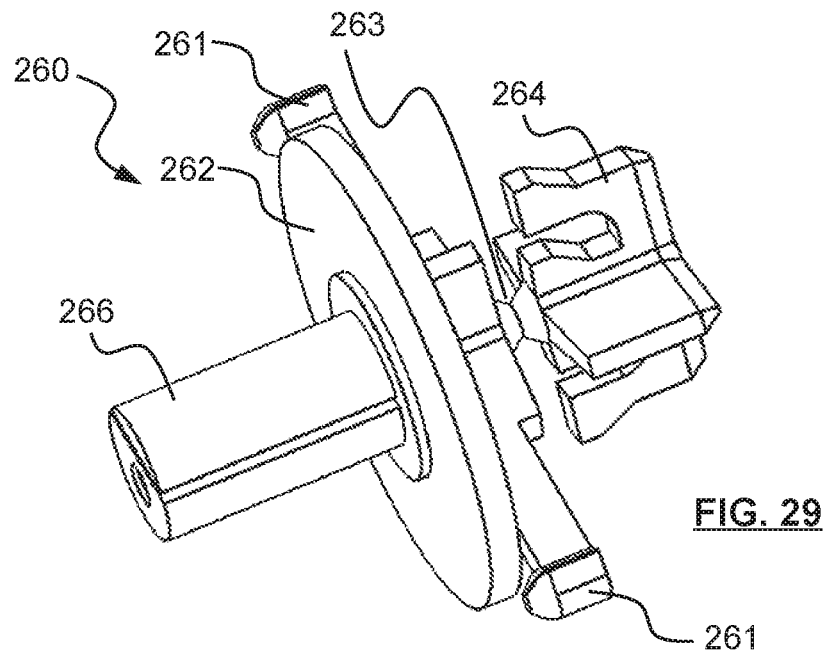
FIG. 29 is a perspective view of the slider of the driving member of the apparatus of FIG. 22 before the stem is broken off.
Figure 30:
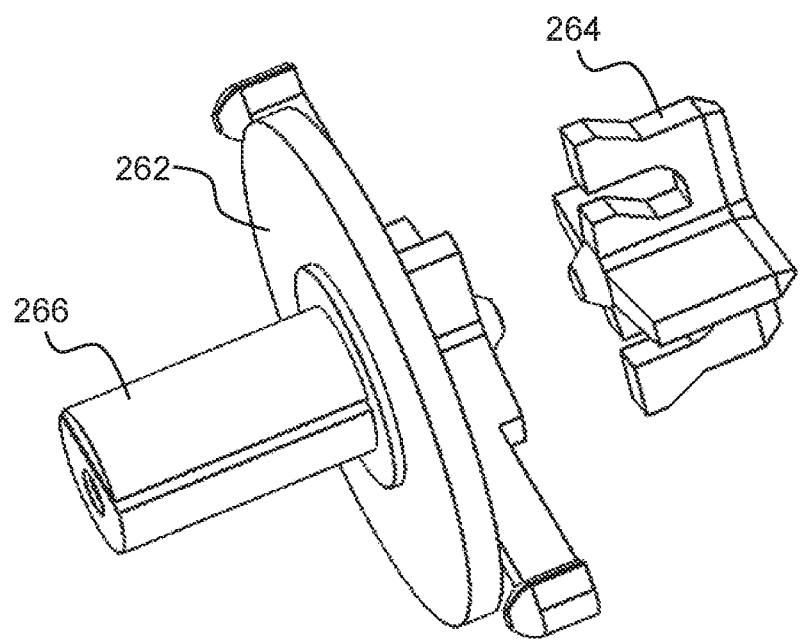
FIG. 30 is a perspective view of the slider of the driving member of the apparatus of FIG. 22 after stem is broken off.

As shown in FIGS. 29 and 30, between the frame 262 and stem 264 there is formed a neck portion 263. Neck portion 263 has a relatively lower strength compared to the stem 264 and frame 262, and is configured to present a lower resistance to shear forces and torsional moments. For example, neck portion 263 may have a cross sectional dimension less than that of the stem 264. As such, neck portion 263 forms a weak, breakable connection between the frame 262 and the stem 264, which can be broken by a rotational twisting of the stem relative to the frame 262.

A pair of winglets 261 are formed on the frame 262 and engaged to housing 210, restricting rotational movement of the frame 262 relative to housing 210, hence accentuating the torsional forces on the neck 263 via the stem 264.

When the apparatus 200 is at an unused state (FIG. 27), e.g. during the shipment and/or storage period, the driving member 220 may be positioned adjacent to the front end 202 of the housing 210, at which, the spiral spring 250 is at uncoiled or less-coiled state.

Figure 34A:
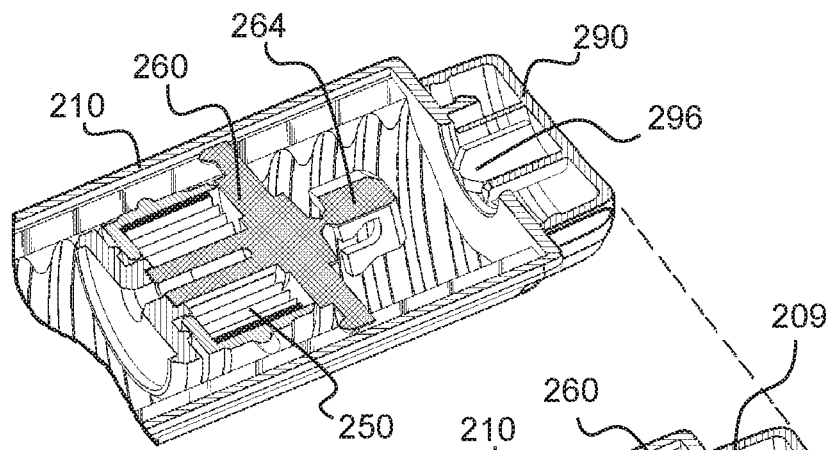
FIG. 34A is an enlarged partial cross sectional view of FIG. 33 showing the driving member moving toward the back end of the housing.
Figure 34B:
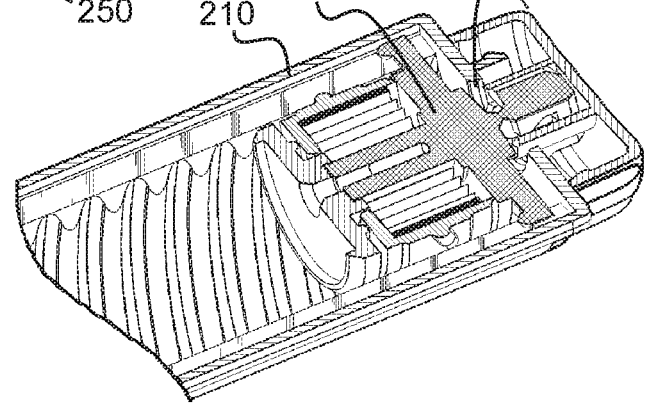
FIG. 34B is an enlarged partial cross sectional view of FIG. 33 showing the driving member reached the back end of the housing and engaged and locked to the knob.

In use, driving member 220 is moved along the axial direction 208 of housing 210 toward the back end 206 of housing 210 (FIG. 28), during which, the casing 240 is rotated to wind the spiral spring 250 to store potential energy in the spiral spring 250. Upon the driving member 220 reaching the back end 206 of the housing 210, as shown in FIGS. 33, 34A and 34B, the stem 264 is positioned to pass through the back opening 209 of the housing 210, and is inserted into and locked to the knob 290 by the tubular catch 296.

Figure 34C:
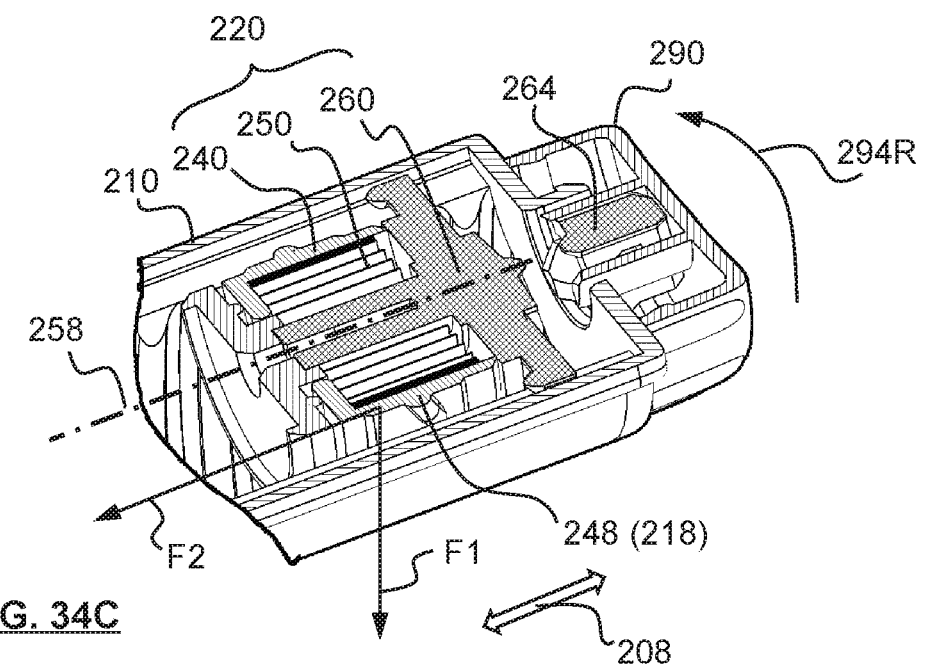
FIG. 34C is an enlarged partial cross sectional view showing the stem being broken off from the casing.

As shown in FIG. 34C, when the stem 264 is broken from the slider 260, by a user twisting the knob 290 relative to the housing 210 along rotational direction 294R, the slider 260 is unlocked from the housing 210. As such, the spiral spring 250 is allowed to release the potential energy stored therein. The spiral spring 250 produces a torque about its own axis, i.e. spring axis 258, which generates a force F1 exerting against the casing 240 along peripheral direction. As the casing 240 is movably coupled to the housing 210 via the engagement of the ridge 248 and the helical groove 218, the peripheral force F1 is converted into an axial force F2 along axial direction 208, to cause displacement of the driving member 220 in the axial direction 208 of the housing 210.

In other words, the axial displacement of the driving member 220 arising from a rotational movement of the casing 240 serves to push the plunger of a syringe attached to the housing 210 for infusion operation, as illustrated in further detail hereinafter.

Vane 2642 maybe formed adjacent to stem 264 to abut against the housing 210 (210b), to ensure the positioning of slider 260 when reaching the back end 206 of the housing 210.

Figure 35:
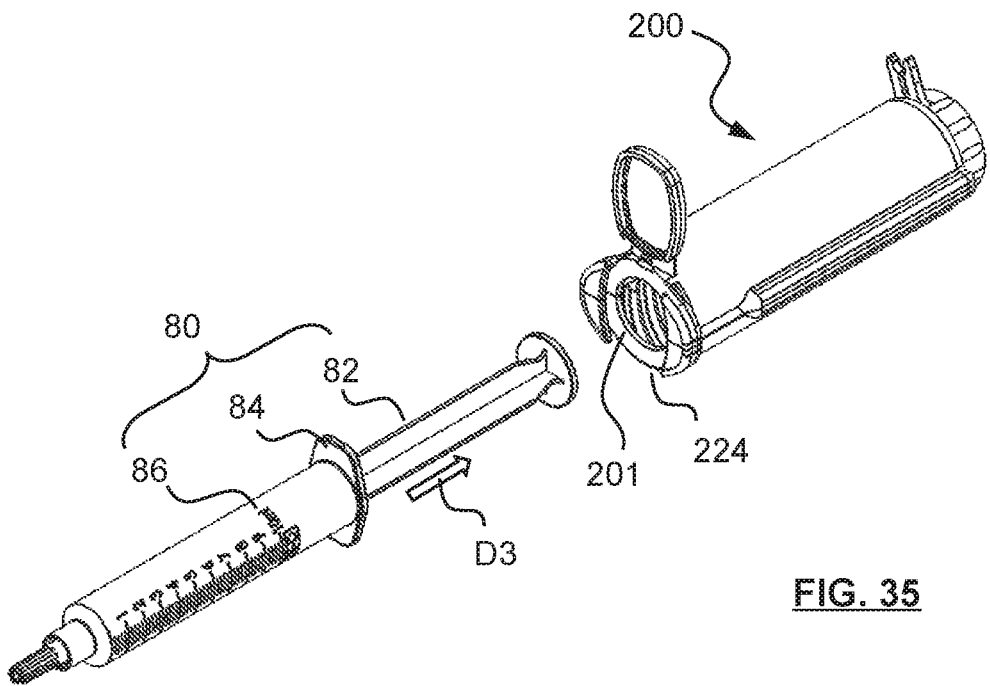
FIG. 35 is a perspective of the apparatus of FIG. 22 ready for receiving a syringe.
Figure 36:
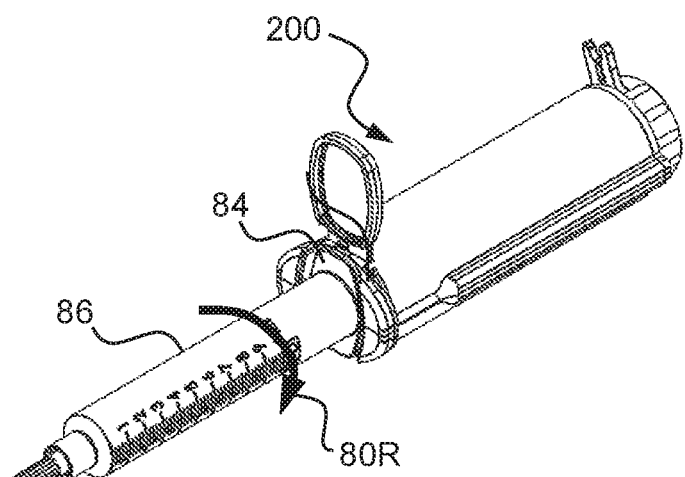
FIG. 36 is a perspective of the apparatus of FIG. 22 when a plunger of a syringe is inserted into the housing of the apparatus.
Figure 37A:
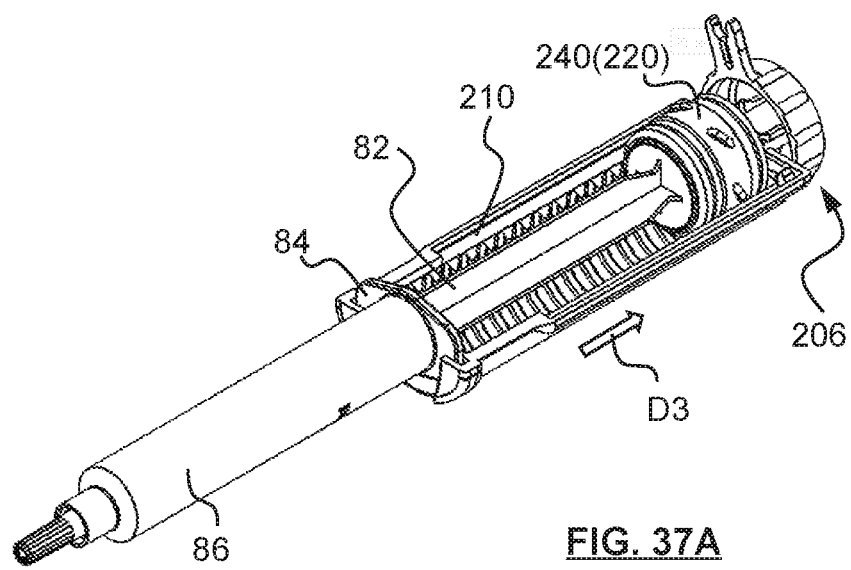
FIG. 37A is a perspective of the apparatus of FIG. 22 showing a plunger of a syringe inserted into the housing of the apparatus and omitting the top portion of the housing.
Figure 37B:
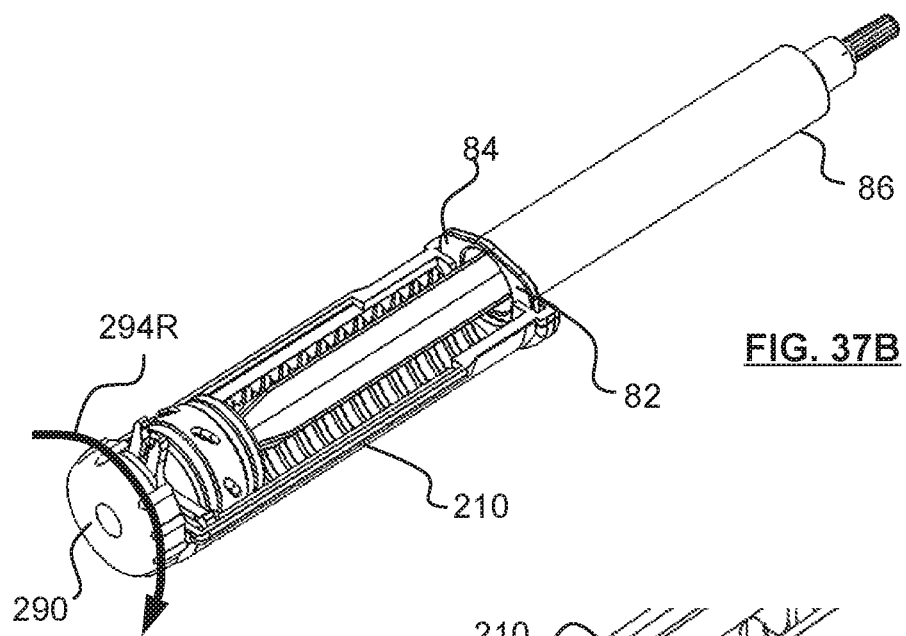
FIG. 37B is a perspective back view of FIG. 37A.
Figure 38:
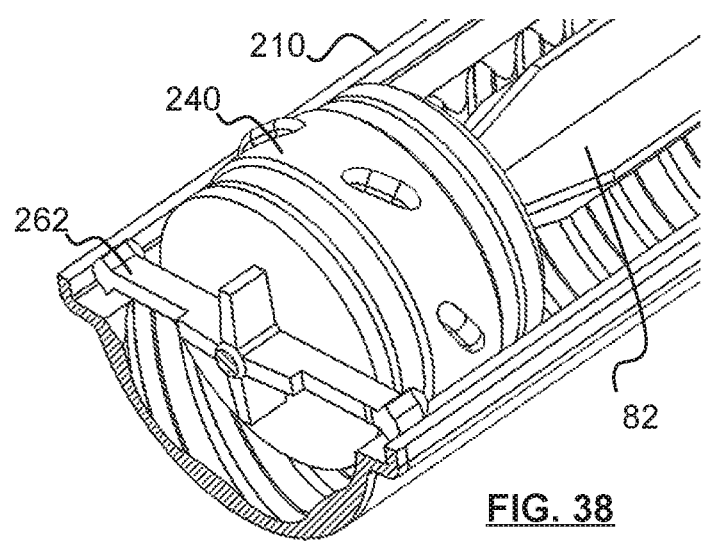
FIG. 38 is a partial enlarged cross sectional view of FIG. 37B omitting the knob.
Figure 39:
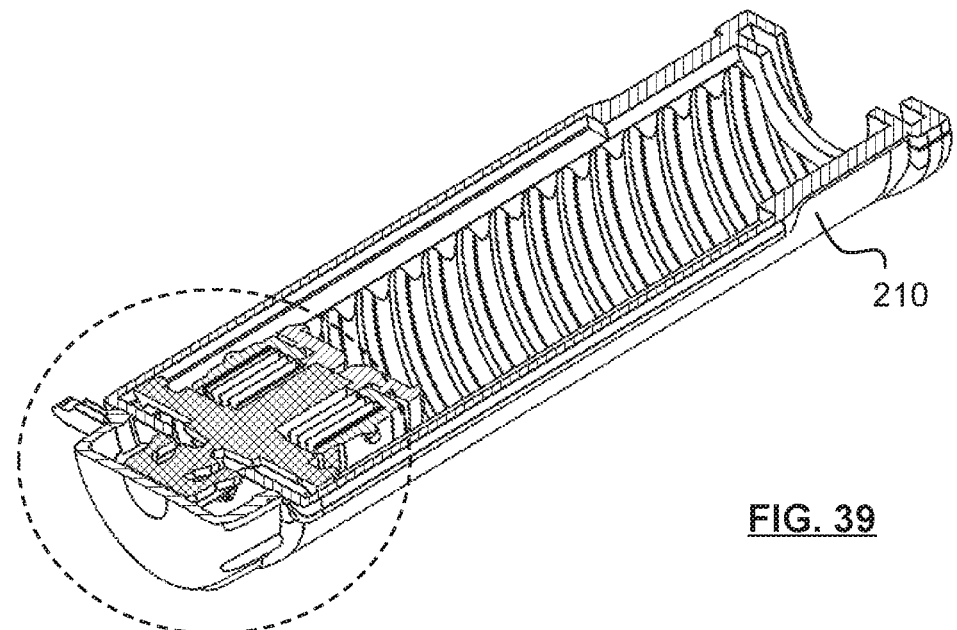
FIG. 39 is a perspective cross sectional view of FIG. 37B showing the knob.
Figure 40:
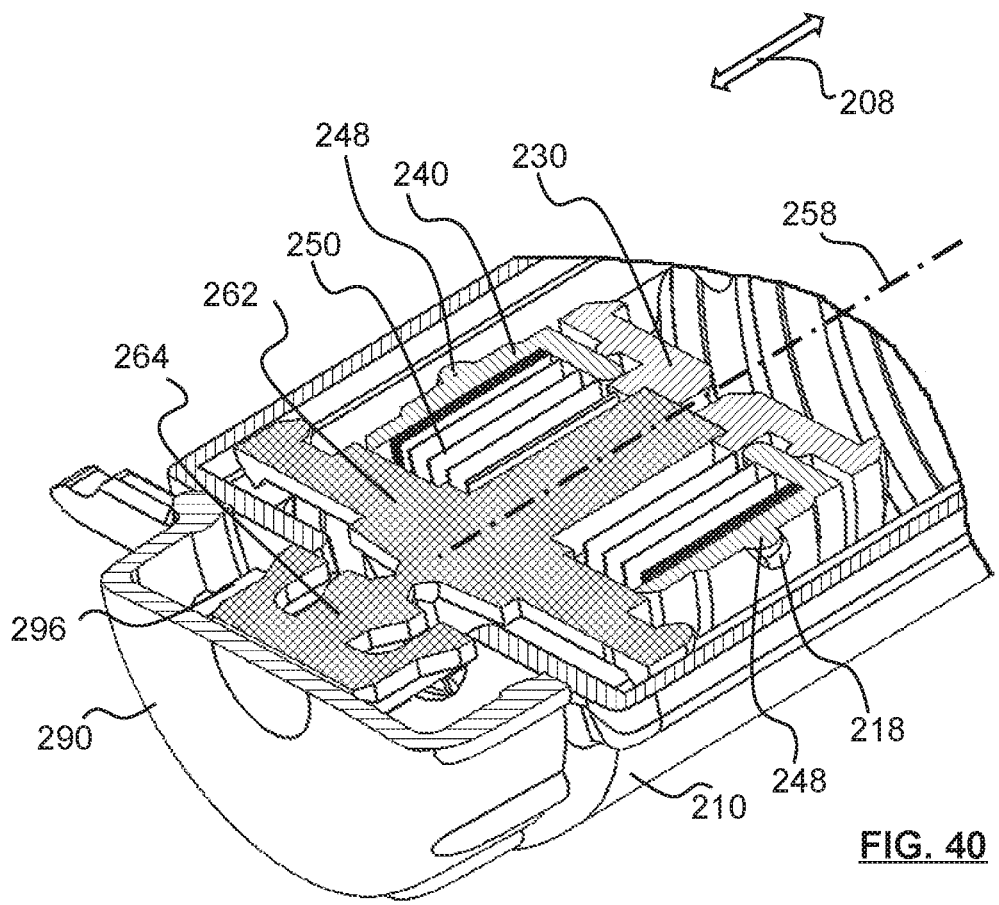
FIG. 40 is an enlarged partial view of FIG. 39.
Figure 41:
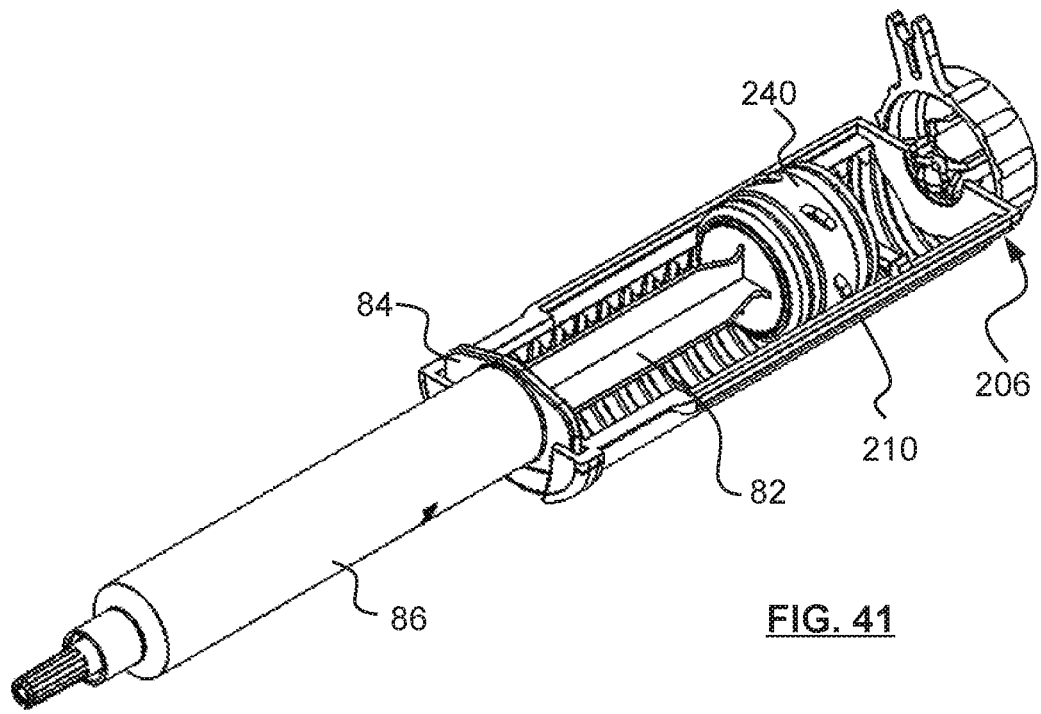
FIG. 41 is a perspective view showing the apparatus of FIG. 22 with a syringe attached thereto and ready for infusion operation via the syringe.
Figure 42:
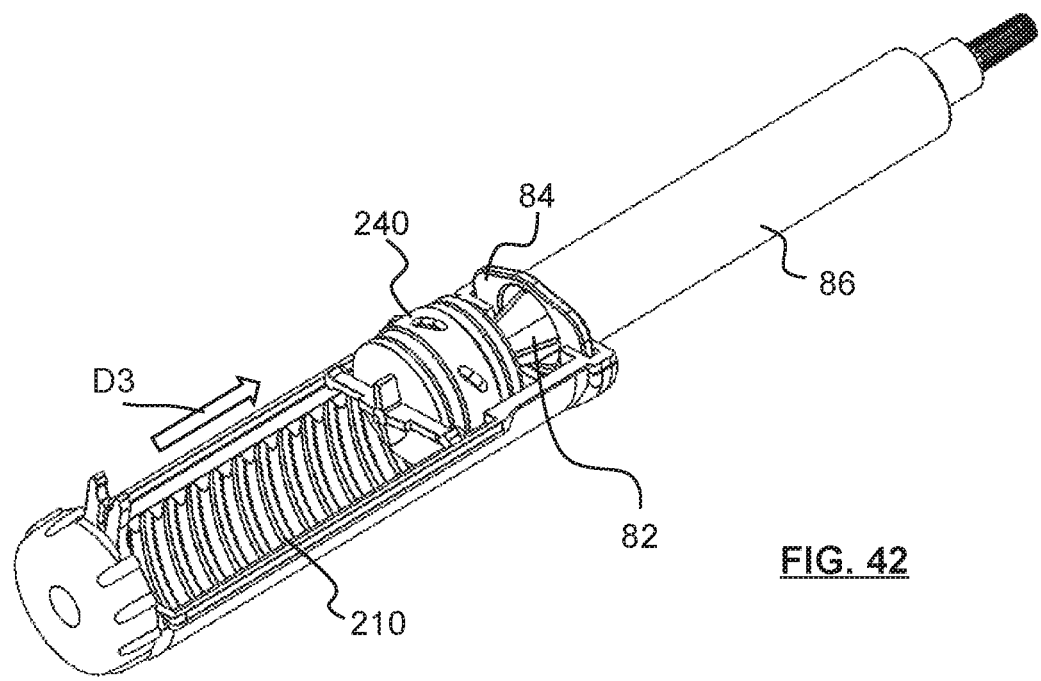
FIG. 42 is a perspective view showing the apparatus of FIG. 22 with a syringe attached thereto and after completion of the infusion operation.

As shown in FIGS. 35 and 36, when it is desired to carry out infusion operation, a syringe 80, which is fully or partially filled with liquid medication, is attached to the apparatus 200 with the plunger 82 placing through the front opening 201 at the front end 202 of the housing 210, along axial direction D3, and with the plunger 82 brought into abutment with the driving member 220. Further advancement of the plunger 82 along axial direction D3 into the housing 210 presses against the driving member 220, to move the driving member 220 towards the back end 206 of the housing 210, along the axial direction 208 of housing 210.

The generally oval shaped flange 84 of the syringe barrel 86 is rotated to become aligned with the retaining portion 224 surrounding the front opening 201. When flange 84 is brought into contact with the rim of the front opening 201, the flange 84 is rotated along circular direction 80R, to position into the groove 204a of the retaining portion 224 to attach the syringe 80 to the apparatus 200.

The dimension of the housing 210 and the driving member 220 are configured in a manner such that when the plunger 82 is fully received in the housing 210, the driving member 220 is positioned at the back end 206 of the housing and engaged with the knob 290, and abuts against the plunder 82. Syringe 80 is now ready for infusion operation.

To start infusion, a user twists (along direction 294R, FIG. 37B) the knob 290 relative to the housing 210, to break the stem 264 at the neck 263. The casing 240, spiral spring 250 and frame 262 are therefore detached from the stem 264. To assist in easy operation to break the stem 264, the winglets 267 formed at the sides of the frame 262 engages to the slots 217 formed on the housing 210 that cross the grooves 218 of the inner walls of the housing 210, to prevent the frame 262 from rotating during the twisting of the stem 264.

Once the stem 264 is broken, the casing 260 is unlocked from the housing 210, to allow the potential energy stored in the spiral spring 250 to release, by which, the casing 260 is driven by the spiral spring 250 to push the plunder 82 into the barrel 86 to expel the liquid medicine from the syringe 80 for infusion.

Although embodiments of the present disclosure have been illustrated in conjunction with the accompanying drawings and described in the foregoing detailed description, it should be appreciated that the present disclosure is not limited to the embodiments disclosed. Therefore, the present disclosure should be understood to be capable of numerous rearrangements, modifications, alternatives and substitutions without departing from the spirit of the disclosure as set forth and recited by the following claims.

I claim:

1. A syringe driving apparatus comprising:
    a housing to which a syringe is attachable, the housing having a front end, a back end and a compartment between the front end and the back end, the compartment is configured to receive a plunger of the syringe therein;
    a driving member disposed in the compartment, the driving member being movable relative to the housing between the front end and the back end;
    a resilient member connected to the housing and the driving member,
    wherein movement of the driving member towards the back end deforms the resilient member to store potential energy in the resilient member,
    upon release of the potential energy, the resilient member moves the driving member towards the front end to press the plunger to expel medicine out of the syringe, and
    wherein the driving member includes a casing and a slider rotatably coupled to the casing, the casing being rotatably and slidably coupled to the housing, the slider being slidably coupled to the housing, wherein the resilient member is a spiral spring having an inner end connected to the slider and an outer end connected to the casing, wherein movement of the slider along an axial direction of the housing towards the back end causes the casing to rotate to wind the spiral spring to store potential energy in the spiral spring, and upon release of the potential energy, the spiral spring unwinds to move the casing along an axial direction towards the front end to press the plunger.

2. The syringe driving apparatus of claim 1, further comprising a locking member connected to the driving member and engageable to the housing to secure the driving member at the back end of the housing.

3. The syringe driving apparatus of claim 2, wherein the locking member is separable from the driving member to release the driving member from the housing.

4. The syringe driving apparatus of claim 3, further comprising a neck portion between the locking member and the driving member, wherein the locking member is separable from the driving member at the neck portion.

5. The syringe driving apparatus of claim 1, wherein the resilient member is an elastic band having a first portion affixed to the housing and a second portion abutting against the driving member, wherein movement of the driving member towards the back end stretches the elastic band to store potential energy in the elastic band, and upon release of the potential energy, the elastic band shrinks to move the driving member towards the front end to press the plunger to expel medicine out of the syringe.

6. The syringe driving apparatus of claim 1, further comprising a seat member movably coupled to the casing to receive the plunger.

7. The syringe driving apparatus of claim 6, wherein the casing having ridges formed on an outer surface thereof, the housing having helical grooves formed on an inner surface thereof, wherein the casing is rotatably and slidably coupled to the casing via an engagement of the ridges and the helical grooves.

8. The syringe driving apparatus of claim 7, wherein the spiral spring winds and unwinds with respect to a spring axis parallel to the axial direction, and wherein the spiral spring unwinds to generate a first force exerting against the casing along a peripheral direction, and the first force is converted into a second force.

9. The syringe driving apparatus of claim 1, further comprising a locking member connected to the slider and a knob coupled to the housing to engage the locking member to secure the driving member at the back end of the housing.

10. The syringe driving apparatus of claim 9, wherein the knob is rotatable relative to the housing to break the locking member from the slider to release the potential energy.

11. An apparatus comprising:
a housing having a front end and a back end;
a driving member disposed in the housing, the driving member being movable relative to the housing between the front end and the back end;
a resilient member connected between the housing and the driving member,
a locking member coupled to the housing to fix the driving member at the back end;
wherein movement of the driving member towards the back end deforms the resilient member to store potential energy in the resilient member,
wherein disengagement of the locking member from the housing releases the potential energy to cause the driving member to move towards the front end, and
wherein the driving member includes a casing and a slider rotatably coupled to the casing, the casing being rotatably and slidably coupled to the housing, the slider being slidably coupled to the housing, wherein the resilient member is a spiral spring having an inner end connected to the slider and an outer end connected to the casing, wherein movement of the slider along an axial direction of the housing towards the back end causes the casing to rotate to wind the spiral spring to store potential energy in the spiral spring, and upon release of the potential energy, the spiral spring unwinds to move the casing along an axial direction towards the front end to press the plunger.

12. The apparatus of claim 11, wherein the locking member is connected to the driving member during the movement of driving member towards the back end, and separated from the driving member to allow the driving member to move towards the first end.

13. The apparatus of claim 11, wherein the resilient member is an elastic band having a first portion affixed to the housing and a second portion abutting against the driving member, wherein movement of the driving member towards the back end stretches the elastic band to store potential energy in the elastic band, and upon release of the potential energy, the elastic band shrinks to move the driving member towards the front end to press the plunger to expel medicine out of the syringe.

14. The apparatus of claim 11, further comprising a seat member movably coupled to the casing to receive the plunger.

15. The apparatus of claim 14, wherein the casing having ridges formed on an outer surface thereof, the housing having helical grooves formed on an inner surface thereof, wherein the casing is rotatably and slidably coupled to the casing via an engagement of the ridges and the helical grooves.

16. The apparatus of claim 15, wherein the spiral spring winds and unwinds with respect to a spring axis parallel to the axial direction, and wherein the spiral spring unwinds to generate a first force exerting against the casing along a peripheral direction, and the first force is converted into a second force.

17. The apparatus of claim 11, further comprising a knob coupled to the housing to engage the locking member to secure the driving member at the back end of the housing.

18. The apparatus of claim 17, wherein the knob is rotatable relative to the housing to break the locking member from the slider to release the potential energy.

* * * * *